(12) United States Patent
Shi et al.

(10) Patent No.: US 12,275,924 B2
(45) Date of Patent: Apr. 15, 2025

(54) METHOD AND DEVICE FOR DETECTING CIRCULATING TUMOR CELL

(71) Applicant: SHANGHAI JIAOTONG UNIVERSITY, Shanghai (CN)

(72) Inventors: Qihui Shi, Shanghai (CN); Shun Lu, Shanghai (CN); Yuliang Deng, Shanghai (CN); Yin Tang, Shanghai (CN)

(73) Assignee: SHANGHAI JIAOTONG UNIVERSITY, Shanghai (CN)

( * ) Notice: Subject to any disclaimer, the term of this patent is extended or adjusted under 35 U.S.C. 154(b) by 127 days.

(21) Appl. No.: 17/377,956

(22) Filed: Jul. 16, 2021

(65) Prior Publication Data
US 2024/0228921 A1    Jul. 11, 2024

Related U.S. Application Data

(62) Division of application No. 15/749,126, filed as application No. PCT/CN2016/080789 on Apr. 29, 2016, now Pat. No. 11,098,274.

(30) Foreign Application Priority Data

Jul. 31, 2015    (CN) .......................... 201510466462.7

(51) Int. Cl.
  *C12M 1/34*    (2006.01)
  *C12Q 1/02*    (2006.01)
  *G01N 33/569*    (2006.01)
  *G01N 33/574*    (2006.01)

(52) U.S. Cl.
  CPC ................. *C12M 1/34* (2013.01); *C12Q 1/02* (2013.01); *G01N 33/569* (2013.01); *G01N 33/57492* (2013.01); *G01N 2333/70589* (2013.01)

(58) Field of Classification Search
  None
  See application file for complete search history.

(56) References Cited

PUBLICATIONS

Cai, Huawei; Peng, Fangyu; 2-NBDG Fluorescence Imaging of Hypermetabolic Circulating Tumor Cells in Mouse Xenograft model of Breast Cancer Journal of Fluorescence, 23, 213-220, 2013 (Year: 2013).*

* cited by examiner

*Primary Examiner* — David W Berke-Schlessel
(74) *Attorney, Agent, or Firm* — Adam Warwick Bell; Matthew Rupert Kaser

(57) ABSTRACT

Provided are a method for detecting a free rare tumor cell in a human biological fluid sample and assay kit. Specifically, the method of the invention determines the existence of an active tumor cell in a biological fluid sample of a cancer patient by detecting and confirming the existence of glucose absorption capability of a karyocyte and expression of a leukocyte marker (CD45).

10 Claims, 8 Drawing Sheets

Specification includes a Sequence Listing.

| cell line | organ | mean cell diameter (micron) | capture rate of ISET (%) | the capture of antibody | capture rate of fishbone chip (%) |
|---|---|---|---|---|---|
| HCT116 | colon cancer | 13.7 | 79±4 | EpCAM | 90±3 |
| MCF7 | breast cancer | 18.1 | 86±2 | EpCAM, HER2 | 85±3 |
| A549 | non-small cell lung cancer | 17.3 | 88±6 | EpCAM, EGFR | 72±5 |
| H1975 | non-small cell lung cancer | 22.1 | 95±5 | EpCAM, EGFR | 94±4 |
| 143B | osteosarcoma | 20.8 | 92±5 | Vimentin | 62±3 |
| Saos-2 | osteosarcoma | 27.3 | 97±3 | Vimentin | 80±5 |

METHOD AND DEVICE FOR DETECTING CIRCULATING TUMOR CELL

TECHNICAL FIELD

The present invention relates to the field of biological and medical detection. More specifically, the present invention relates to a detection method and device for the metabolic activity of circulating tumor cells in human peripheral blood. The method and device of the present invention can perform metabolic function typing on CTC captured in the human peripheral blood and can be used to predict the degree of malignancy of these CTC.

SEQUENCE LISTING

A sequence listing text (.txt) file is submitted herewith under 37 CFR. 1.821 (c) and is hereby incorporated by reference in its entirely. The details of the file as required under 37 CFR. 1.52 (e) (5) and 37 CFR 1.77(b)(5) are as follows: Name of file is "XU-P2021-1853 sequence listing.txt"; date of creation is Aug. 21, 2022; size is 482 bytes. The content of the sequence listing information recorded in computer readable form is identical to the written sequence listing (if any) and identical to the sequence information provided with the original filed application and with the priority application, and contains no new matter. The information recorded in electronic form (if any) submitted (under Rule 13ter, if appropriate) with this application is identical to the sequence listing as contained in the application as filed.

BACKGROUND

The circulating tumor cells (CTC) in the human peripheral blood refer to the tumor cells that spread from the tumor focus into the peripheral blood circulation and can develop into metastatic tumor focus under a certain condition. Since more than 90% of cancer deaths are caused by metastases, whereas CTC is a direct source of tumor metastasis, therefore, the separation of the CTC from the blood and molecular detection therefor has attracted an increasing attention. However, CTC is extremely rare in the blood. One milliliter of blood contains 5 billion red blood cells and nearly 10 million white blood cells, but it only has several to several tens of CTCs, thereby bringing a great technical challenge for the detection.

At present, the basic strategy for the detection of CTC is to enrich and then identify, mainly to count all the CTCs in the peripheral blood of cancer patients. However, only counting the entire CTCs cannot fully and accurately reflect the current status of tumor focus and the risk of metastases. The reason of which lies in the fact that the study has found that CTC has a great functional heterogeneity. A significant proportion of CTCs is in an apoptotic state, and only a small proportion of CTCs can achieve metastasis. This is consistent with the clinical observations. Therefore, what needs to be really focused on in clinic is a small proportion of CTCs with high level of vitality and metastatic potential. At present, studies have been conducted for the clinical research to explore the application of CTC by using the number of active CTCs (identification of the activity of cells by dyes for the living cells or secretory proteins) or the ratio of live CTCs to total CTCs as marker, but the cell viability itself is still less correlated with the degree of malignancy of tumor cells. At present, there is still a lack of technology and equipment for testing CTC function to determine the degree of malignancy and the metastasis possibility of CTC.

In addition, the current detection method for CTC basically adopts the strategy of enriching CTC in blood and then performing detection, such as the CellSearch system, but this type of CTC detection method has several defects. Firstly, the enrichment method of the CellSearch system is not sensitive enough, the detection rate is low, and a considerable part of the CTC is lost during the enrichment process. Secondly, this method is based on the tumor cell identification for EpCAM+/DAPI+/CK+/CD45− and does not use any tumor-specific markers. Actually the epithelial-derived cells but not tumor cells are identified, and the latest research shows that epithelial-derived cells can also be detected in the blood from patients with benign disease and even healthy people, so there is a possibility of false positives for this method of identification. At the same time, studies have found that epithelial-mesenchymal transition (EMT) of tumor cells that occurs during metastasis will result in non-expression of CTCs or low expression of epithelial markers and may be missed. Thirdly, because fixation and nuclear staining are used in the immunofluorescent staining-based CTC identification method described above, it is difficult for the CTCs after immunofluorescence staining to be further used for sequencing analysis and in vitro culture, whereas sequencing is currently the most important molecular detection method for tumors. Single cell sequencing for CTCs can further clarify the properties of tumor cells and identify molecular targets for targeted drug therapy by sequencing the driver genes, while fixation and nuclear staining will interfere with genomic amplification for a single cell, thereby affecting the follow-up sequencing. Therefore, it should keep the activity of the cells as much as possible and the steps for identifying the CTCs does not include steps that affect the amplification of a single-cell genome, such as immobilization. Fourthly, the study has found that CTCs have a great functional heterogeneity. A considerable number of CTCs are in apoptotic or necrotic state. Only a part of CTCs are able to achieve metastasis, and those CTCs with highly activity and metastatic potential rather than all CTCs are really clinically needed to be paid attention to. Technologies, including CellSearch, cannot functionally identify the degree of malignancy and metastatic potential of CTCs.

At present, almost all the CTC detection methods have similar defects with the CellSearch system. The enrichment procedures are cumbersome and complicated, and the CTCs are lost. However, the immunofluorescence staining-based CTC identification method can not accurately identify tumor cells, and the subsequent gene sequencing analysis and in vitro culture are limited. Therefore, there is an urgent need in the art to develop techniques capable of effectively and rapidly detecting CTCs with a high degree of activity and malignancy, in particular, to develop techniques capable of rapidly and accurately identifying the tumor cells with a high degree of activity and malignancy in tumor patient's peripheral blood or pleural fluid samples, and this technology does not affect the subsequent sequencing or in vitro culture for the identified tumor cells.

SUMMARY OF THE INVENTION

The object of the present invention is to provide a method and detection equipment, which can effectively and rapidly detect the degree of malignancy of free CTCs in the blood from a tumor patient, without affecting the subsequent sequencing or in vitro culturing for the identified tumor cells.

Based on the above needs, the innovations of the present invention mainly include the following items: Firstly, the enrichment step is not used so as to greatly reduce the loss of CTCs. The enrichment herein refers to the enrichment of nucleated cells, and the blood components such as platelets, and non-nuclear red cells which are not confounded with CTC, can still be removed. Secondly, tumor cells can quickly be identified in all nucleated cells by a simple and effective method. Due to simple and rapid method of identification, it can ensure that a large number of cells can be detected, making it possible to perform direct detection without enrichment. Thirdly, the detection method of tumor cells does not affect subsequent sequencing and in vitro culture. Fourthly, all cells can be addressed, so that individual tumor cell can be easily and accurately removed for the sequencing.

The method for identifying tumor cells used in the present invention (high glucose uptake and no white blood cell common antigen CD45 expressed on cell surface are the universal features of tumor cells) does not depend on the size of tumor cells, the expression of surface antigens, etc., and therefore it is a simple and reliable way to identify tumor cells. Due to simplicity and speed, it combined with the high-speed fluorescence imaging system can rapidly detect a large number of cells, making it possible not to enrich nucleated cells in a sample. At the same time, glucose uptake and CD45 detection do not affect cell viability, and can be used for subsequent single-cell genome sequencing and in vitro culture. The cells are arranged in an addressable manner so that the tumor cells can be easily found and taken out.

In the first aspect of the present invention, a method for non-diagnostically detecting metabolic activity of circulating tumor cells is provided, comprising the steps of:
  (a) enriching and isolating a circulating tumor cell CTC from a peripheral blood sample, thereby obtaining the isolated circulating tumor cell CTC;
  (b) placing the circulating tumor cell isolated in the above step in a microwell array chip, so that there is at most one circulating tumor cell in each microwell of the microwell array chip;
  (c) resuscitating the circulating tumor cell in the above step, thereby obtaining the resuscitated circulating tumor cell;
  (d) culturing the resuscitated circulating tumor cell in the presence of a glucose analogue carrying a detectable label; and
  (e) detecting uptake of the glucose analogue carrying the detectable label by the circulating tumor cell to qualitatively or quantitatively determine metabolic activity and/or malignancy degree of the circulating tumor cell.

In another preferred embodiment, a high intake of the glucose analogue means that the circulating tumor cell has a high degree of malignancy.

In another preferred embodiment, between steps (c) and (d), it further comprises the step of starving the resuscitated circulating tumor cell.

In another preferred embodiment, in step (c), in the resuscitation process, it further comprises adding a fluorescent modified antibody (such as anti-CD45-FITC) against leukocyte surface antigens to recognize leukocyte, thereby distinguishing the CTC from leukocytes In another preferred example, in step (c), in the resuscitation treatment, it further comprises adding bovine serum albumin to block a cell and a microwell chip, thereby eliminating non-specific adsorption of 2-NBDG.

In another preferred embodiment, in step (c), a dead cell dye (eg, EthD-1, ethidium homodimer-1) is added during the resuscitation process to identify the dead cell.

In another preferred embodiment, the starvation treatment is to place the circulating tumor cell under the culture conditions of low glucose concentration or glucose-free for a period of time.

In another preferred embodiment, the starvation treatment is performed for 1-60 minutes, preferably 2-30 minutes, more preferably 5-20 minutes.

In another preferred example, the resuscitation process comprises one or more selected from the group consisting of:
  (i) resuscitation in a physical environment, wherein the physical environment refers to a low oxygen environment, i.e., oxygen volume fraction is below 10%;
  (ii) resuscitation in a chemical environment, wherein the chemical environment refers to culture in a cell culture medium containing a cytokine, wherein the cytokine comprises an epidermal growth factor, a fibroblast growth factor, or a combination thereof;
  (iii) resuscitation in a tumor cell culture supernatant.

In another preferred embodiment, the detectable label comprises a chemically modified group.

In another preferred embodiment, the detectable label comprises a fluorescent group, biotin.

In another preferred embodiment, the glucose analogue carrying a detectable label is 2-NBDG.

In another preferred embodiment, the peripheral blood sample is a sample from a mammal (such as human).

In another preferred embodiment, in step (a), enrichment and isolation of the circulating tumor cell from peripheral blood is performed by an immunomagnetic bead method, wherein the immunomagnetic bead is loaded with an antibody that specifically binds to a tumor surface antigen.

In another preferred example, in step (a), isolation is performed by a fishbone chip isolation capture method.

In another preferred example, in step (a), isolation is performed using a fishbone chip of the structure as shown in FIG. 4.

In another preferred embodiment, the number of circulating tumor cell CTC enriched and isolated from the peripheral blood sample in step (a) is n1; in step (b), the number of microwells of the microwell array chip is n2, and the ratio of n2/n1 is ≥10.

In another preferred embodiment, the ratio of n2/n1 is ≥20, more preferably, the ratio of n2/n1 is ≥100.

In another preferred embodiment, in step (b), a suspension of the circulating tumor cell obtained in step (a) is added to the microwell array chip, and a magnetic field is applied to make the circulating tumor cell into microwells, thereby ensuring that the glucose uptake test sample is not lost.

In another preferred embodiment, in step (e), the excess glucose analog is washed, and then the ability of glucose uptake by the circulating tumor cell is characterized according to the signal of the glucose analog uptaken into the circulating tumor cell.

In another preferred embodiment, the process of cleaning the excess glucose analog is performed under the application of a magnetic field, thereby ensuring that the circulating tumor cell is immobilized on the substrate so as not to be eluted.

In another preferred embodiment, in steps (b) to (e), the cell surface of the circulating tumor cell is bound with a magnetic bead.

In another preferred embodiment, the surface of the isolated circulating tumor cell CTC is combined with an immunomagnetic bead.

In another preferred embodiment, in step (d), the glucose analog is co-cultured with the circulating tumor cell for a period of 2 minutes to 2 hours, more preferably, 5 minutes to 1 hour.

In another preferred embodiment, in step (e), the amount of glucose analog uptaken into the circulating tumor cell is detected by a fluorescent signal or a spectral signal.

In another preferred embodiment, in step (a), the peripheral blood sample is (i) a peripheral blood sample without any treatment; or (ii) a peripheral blood sample without treatment of removing a red blood cell and/or without treatment of removing leukocyte.

In another preferred embodiment, the peripheral blood sample is a peripheral blood sample that has been centrifuged to remove platelets and plasma.

In another preferred embodiment, in step (e), it further comprises: comparing with a reference value or a standard curve to qualitatively or quantitatively determine the metabolic activity level of the circulating tumor cell.

In the second aspect of the present invention, adevice for detecting metabolic activity of the circulating tumor cell is provided, comprising:
(a) a fishbone chip;
(b) a microwell array chip;
(c) a first container, and a glucose analogue carrying a detectable label placed in the first container;
(d) an optional magnetic bead for capturing the circulating tumor cell, which is loaded with an antibody that specifically binds to a tumor surface antigen; and
(e) an optional magnetic field device, comprising a permanent magnet or an electromagnet.

In another preferred embodiment, the device further comprises:
(f) a second container, and a sealing agent (such as bovine serum albumin) in the second container.

In another preferred embodiment, the device further comprises:
(g) a third container, and an antibody for discriminating between a circulating tumor cell and a leukocyte within the third container, such as a fluorescently modified antibody (eg, anti-CD45-FITC) against a leukocyte surface antigen.

In another preferred embodiment, the device further comprises:
(h) a fourth container, and a dead cell dye (eg, EthD-1, ethidium homodimer-1) in the fourth container for identifying a dead cell.

In another preferred embodiment, the fishbone type chip has the following structure: the chip is provided with an inlet and an outlet, the channel is continuous S-shaped, the width is 1±0.2 mm, the interval between channels is 1±0.2 mm, and the straight side is 30-70 mm in length, with a total of 5-15 straight sides.

In another preferred embodiment, the fishbone type chip has the following structural features: the cross section of the chip presents a periodic concave-convex structure, which is composed of two layers of photoresist, and the upper layer of fishbone patterns are periodically arranged, and the width of the fishbone is 125±20 μm, the horizontal angle is 45±5°, and the periodic interval is 75±10 μm.

In another preferred embodiment, the magnetic beads have a particle size of 1-1000 nm, more preferably 10-500 nm.

In another preferred embodiment, the magnetic beads have a particle size of 1-1000 microns, more preferably 10-500 microns.

In another preferred embodiment, the magnetic beads have a particle size of 1-20 mm, more preferably 1-5 mm.

In the third aspect of the present invention, a method for non-diagnostically detecting a free rare tumor cell in a human biological liquid sample is provided, comprising the steps of:
(a) providing a biological sample of a peripheral blood or a hydrothorax, the biological sample is a sample obtained by selective lysis to remove a red blood cell;
(b) co-incubating the sample in step (a) with a fluorescently modified antibody against leukocyte surface antigen CD45, so that the surface of the leukocyte in the sample is labeled with a fluorescently modified antibody against the leukocyte surface antigen CD45;
(c) dispersing the cell sample labeled with the fluorescently modified antibody against leukocyte surface antigen CD45 obtained in step (b) into the microwell array chip, the chip comprises a plurality of microwells which are used for containing cells and may be addressed, and the ratio of the number of microwells to the number of cells in the sample is 1:0.2-5, preferably 1:1-3;
(d) co-culturing the cells distributed in the microwell arrays with a fluorescently labeled glucose analog;
(e) detecting the uptake of the fluorescently labeled glucose analog by cells in each microwell and fluorescent signals for CD45 expression; and
(f) identifying the cell with high glucose uptake and without expression of CD45 as the active tumor cell and recording the coordinates of the microwell where the cell is located;
and in step (a), the biological sample of the peripheral blood or the hydrothorax is a sample that has not been enriched by nucleated cells.

In another preferred embodiment, the human biological liquid sample is selected from the group consisting of: blood, hydrothorax, pericardial effusion, and more preferably a peripheral blood or hydrothorax sample from a tumor patient. In another preferred embodiment, the tumor cell is a circulating tumor cell (CTC), preferably a tumor cell selected from the group consisting of: liver cancer, lung cancer, gastric cancer, colon cancer, breast cancer, and ovarian cancer.

In another preferred embodiment, in step (a), the peripheral blood sample is a peripheral blood sample that has not been treated to remove leukocyte.

In another preferred embodiment, in step (a), the sample is a sample that has been pretreated by the following step: negatively selecting a leukocyte with an immunomagnetic bead bearing a CD45 antibody to obtain a sample that most of the leukocytes are removed.

In another preferred embodiment, step (c) further comprises: adding bovine serum albumin to seal the microwell chip, thereby eliminating non-specific adsorption of the fluorescently-labeled glucose analogue.

In another preferred embodiment, the starvation treatment is to place the cells in the microwells under the culture conditions of low glucose concentration or glucose-free for a period of time.

In another preferred embodiment, the starvation treatment is conducted for a period of 1-30 minutes, preferably 5-20 minutes, more preferably 10 minutes.

In another preferred embodiment, in step (d), the fluorescently labeled glucose analog is co-cultured with the tumor cells for a period of 5-30 minutes, more preferably 10-20 minutes.

In another preferred embodiment, in step (e), the redundant fluorescently-labeled glucose analog is washed, and then the uptake of the fluorescently-labeled glucose analog of cells in each microwell is detected.

In another preferred embodiment, the fluorescently labeled glucose analog is 2-NBDG.

In another preferred embodiment, in step (e), it further comprises: comparing with a reference value to determine the glucose uptake level of cells in the microwell.

In another preferred embodiment, after step (f), it further comprises: the tumor cells identified as active are removed from the recorded location by manual or automated micromanipulation equipment for further gene sequencing analysis or in vitro culture.

In another preferred embodiment, the number of the microwells on the chip is 50,000 to 500,000, preferably 150,000-250,000.

In another preferred embodiment, the microwell has a diameter of 15-30 microns, preferably 18-25 microns.

In another preferred embodiment, the method further comprises: calculating the number of active tumor cells contained in the sample by identifying the number of the obtained active tumor cells.

In another preferred embodiment, between steps (a) and (b), it further comprises a step of removing leukocytes by immunomagnetic beads labeled with a CD45 antibody to reduce cell number.

In another preferred embodiment, the method further comprises: in step (d), a dead cell dye is added at the same time to mark the necrotic cells; preferably, the dead cell dye is EthD-1.

In another preferred embodiment, after step (f), a step is further included: the tumor cells identified as active are removed from the recorded location by manual or automated micromanipulation equipment for further analysis or culture.

In another preferred embodiment, the fluorescently labeled glucose analog is 2-NBDG.

In another preferred embodiment, the fluorescently modified antibody against the leukocyte surface antigen CD45 is Allophycocyanin, that is, an APC-labeled CD45 antibody.

In another preferred embodiment, the fluorescence of the leukocyte marker CD45 antibody does not interfere with the fluorescences of the fluorescently labeled glucose analog 2-NBDG and the dead cell dye EthD-1.

In another preferred embodiment, the method further comprises: identifying 2-NFDG strongly positive, CD45 negative and EthD-1 negative cells as suspected tumor cells.

In the fourth aspect of the present invention, a kit for detecting a free rare tumor cell in a human biological liquid sample is provided, which comprises:
(a) a microwell array chip, which comprises a plurality of microwells which are used for containing cells and can be addressed;
(b) a fluorescently modified antibody for the leukocyte surface antigen CD45, which is used for labeling leukocytes in a sample;
(c) a glucose analog with a detectable label (preferably a fluorescent-labeled glucose analog), which is used to detect the glucose uptake capacity of cells in the sample;
and optionally (d) a dead cell dye, which is used to label the necrotic cells in the sample.

In another preferred embodiment, the microwell has a diameter of 15-30 microns, preferably 18-25 microns.

In another preferred embodiment, the number of the microwells on the chip is 50,000 to 500,000, preferably 150,000-250,000.

In another preferred embodiment, the glucose analogue carrying a detectable label is 2-NBDG; the fluorescently modified CD45 antibody is an APC marked CD45 antibody, and/or the dead cell dye is EthD-1.

It should be understood that, within the scope of the present invention, each technical feature of the present invention described above and in the following (as examples) may be combined with each other to form a new or preferred technical solution, which is not listed here due to space limitations.

DESCRIPTION OF FIGURE

FIG. 1 shows a schematic diagram of magnetic trapping of a microwell chip CTC according to one example of the present invention. Wherein FIG. 1A shows that the CTC surface combines with antibodies and magnetic spheres. Before the magnetic field is applied, the CTCs are dispersed in the solution; after the magnetic field is applied, the CTCs enter the microwell under the action of the magnetic field, and are dispersed in the independent microwell. FIG. 1B shows a schematic diagram of a microwell array chip and the captured CTC cells.

FIG. 4 shows a schematic diagram of design of a fishbone-like chip according to one example of the present invention. Wherein FIG. 4A shows the structure of the fishbone-like chip: the chip is provided with an inlet and an outlet, the channel is continuous S-type, the width is 1 mm, the spacing between channels is 1 mm, the straight flange is 50 mm in length (9 straight flanges in total), and the cross-section of the chip presents a periodic concave-convex structure made of two 50 μm of SU8 photoresists. The upper fishbone patterns are arranged periodically. The width of the fishbone is 125 μm, the horizontal sextant angle is 45°, and the periodic interval is 75 μm. FIG. 4B shows the prepared fishbone-like chip. FIG. 4C shows an enlarged observation view of the chip under the microscope.

FIG. 5 shows a fluorescent micrograph of five CTCs having 2-NBDG uptake activity isolated from 2 ml of peripheral blood of a stage IV lung cancer patient according to one example of the present invention. Wherein FIG. 5A is a field view of a bright field microscope; FIG. 5B is a field view of a fluorescence field, and cells emit green fluorescence after ingesting 2-NBDG.

DETAILED DESCRIPTION

Figure 1:
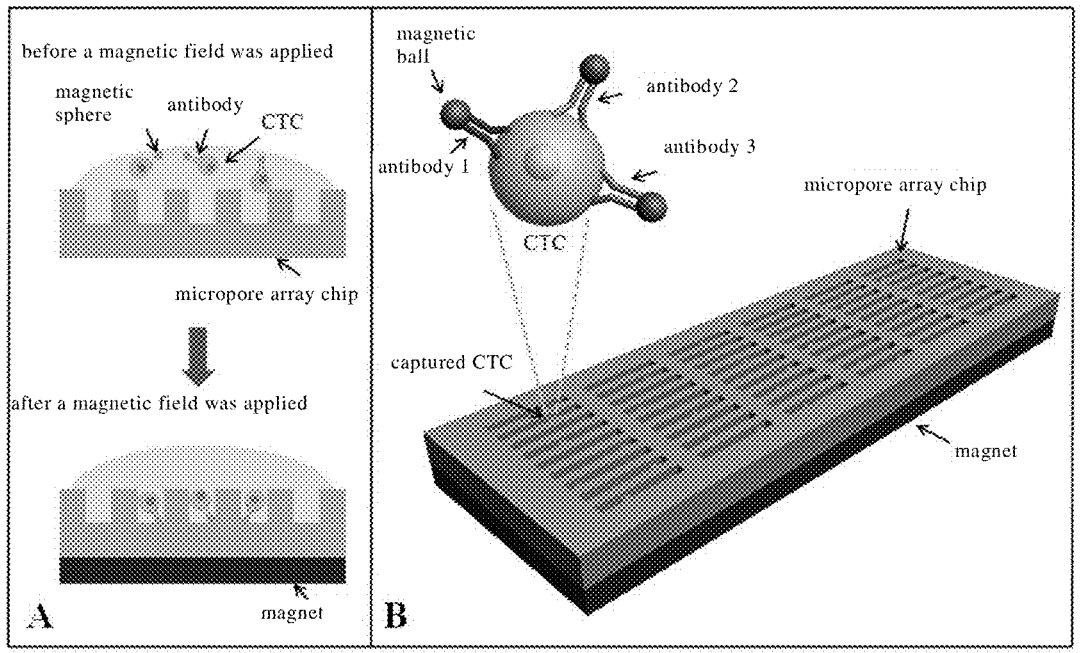

After extensive and intensive studies, the present inventors have for the first time developed a method which can effectively and rapidly detect the degree of malignancy of extremely rare CTCs in the blood. In the method of the present invention, on the one hand, the vitality of CTCs is maintained as much as possible so as to reduce and avoid the loss of CTCs in the process of enrichment and separation, and on the other hand, the CTCs in a dormant state are converted into a non-dormant state by the special treatment, thereby efficiently, quickly and accurately detecting the CTCs with high viability and/or metastatic potential by the determination of the cell uptake level of glucose.

Specifically, in the present invention, CTCs are captured based on methods such as immunomagnetic and the loss or damage of CTCs due to operations such as changing solutions, cleaning, etc. during the metabolic activity detection of CTCs can be avoided by using a micro-control array chip and a magnetic field. In addition, because in vitro separation of CTCs often results in a state of growth inhibition and low metabolic activity, steps such as resuscitation are used to create recovery or promote CTC growth and proliferation, thereby restoring it to be a better state for glucose uptake detection and making the test results more accurate and reliable.

The present inventor has also invented a method and device capable of effectively and rapidly detecting extremely rare tumor cells in a blood or pleural fluid sample of a tumor patient, that is, identifying the active tumor cells in blood or pleural effusion by through the glucose uptake ability and expression of the leukocyte marker CD45 of the cell, and the described method does not require enrichment of tumor cells, so that extremely high accuracy can be achieved.

On this basis, the inventors completed the present invention.

Terms

As used herein, the term "2-NBDG" refers to (2-(N-(7-nitrobenz-2-oxa-1,3-diazol-4-yl)amino)-2-deoxyglucose), which is a fluorescent-labeled glucose analog.

As used herein, the term "EthD-1" refers to Ethidium homodimer-1, i.e., bromoethidium dimer-1, which is a dye that labels necrotic cells.

Circulating Tumor Cell CTC

CTC (Circulating Tumor Cell) refers to a collective name of various types of tumor cells present in the peripheral blood. It is detached from solid tumor lesions (primary lesions, metastasis lesions) due to spontaneous or diagnosis and treatment operations. Most CTCs apoptosis or phagocytosis occurs after most CTCs enter the peripheral blood, while a few CTCs can escape and anchor to develop into metastasis lesions, increasing the risk of death of cancer patients.

In the present invention, CTC cells suitable for the method of the present invention are not particularly limited and may be tumor cells derived from various different solid tumors. Representative examples include (but are not limited to): liver cancer, lung cancer, stomach cancer, colon cancer, breast cancer, ovarian cancer, and the like.

The energy metabolism pathway of tumor cells is mainly glycolysis, which rapidly generates ATP and substances required for biosynthesis by ingesting large amounts of glucose, ensuring that tumor cells can rapidly divide and proliferate.

Detection Method for Glucose Uptake Capacity of Circulating Tumor Cells

The present invention provides a method for detecting the glucose uptake capacity of rare circulating tumor cells in peripheral blood. Typically, it includes the following steps:
  a. Enriching and isolating circulating tumor cells from peripheral blood by immunomagnetic-based methods, so that the surface of the isolated circulating tumor cells is combined with the immunomagnetic;
  b. Placing the isolated circulating tumor cells in a certain cell culture environment;
  c. in the cell culture environment described above, adding a chemical group-modified glucose analog and co-culturing with circulating tumor cells for a period of time;
  d. Washing away the excess glucose analog, and then the glucose uptake ability of the circulating tumor cells is characterized based on the signal of glucose analogs uptaken into circulating tumor cells.

For a better understanding of the present invention, the inventors provide the following mechanism for reference. However, it should be understood that the scope of protection defined by the claims of the present invention is not limited by this mechanism.

In the present invention, a method for in vitro detection of CTC metabolic activity, i.e., glucose uptake capacity is provided based on a biological principle that the ability of glucose uptake capacity for tumor cells is much higher than that for normal cells. The starting point of the method of the present invention is to perform imaging detection of glucose uptake on appropriately processed CTC cells, and by detecting the intensities of glucose uptake of enriched CTCs, functional typing of metabolic activity is performed for CTCs to distinguish between active live CTCs and CTCs that are in apoptotic states, as well as to recognize CTCs with high metabolic activity, then to identify the malignancy degree of CTCs.

In the method of the present invention, the technical challenges and difficulties mainly lie in:
  (1) It is necessary to maintain the activity of CTC as much as possible during the CTC enrichment process, and to reduce the damage to CTC during the enrichment and isolation process. Therefore, in the method of the present invention, blood sample pretreatment methods, such as red blood cell lysis and density gradient centrifugation, which can cause chemical and mechanical damage, should be avoided;
  (2) in vitro isolation of CTC has certain damage to CTC, which makes it in a state of growth inhibition and low metabolic activity. Therefore, in order to better perform functional testing, it is necessary to create a cell culture environment conducive to the normal growth and proliferation of CTC (including physical environment, chemical environment, and biological environment), especially the in vivo microenvironment that mimics the formation of metastasis lesions in target organs by CTCs, enabling CTC to recover to a better state for subsequent functional detection;
  (3) The number of CTCs is very small and can be as few as one. Therefore, during the process of glucose uptake detection, mechanisms are needed to ensure that a very small number of target CTCs will not be lost. However, it is an ideal method to constrain and manipulate CTCs through magnetic fields.

For CTC, it has a variety of different phenotypes, characteristics and metabolic activities. In the present invention, what is detected is the glucose uptake ability of CTC. The present inventors' studies have shown that although the glucose uptake ability of CTC is one of CTC metabolic activity, it is closely related to the activity and malignancy degree of CTC and can more reasonably reflect the vitality and/or malignancy degree of CTC cells.

In contrast, other methods for detecting CTCs currently focus on the number of CTCs, gene mutations, and protein markers, instead of a direct characteristic for the actual functions of CTCs. Therefore, it is difficult to effectively distinguish between live CTCs and CTCs that are in an apoptotic state, to characterize functional heterogeneity among CTCs, and it is difficult to identify highly active and malignant CTC subpopulations.

In the present invention, the CTCs with high vitality and/or metastatic potential can be efficiently and accurately detected by the special resuscitation treatment and starvation treatment.

Resuscitation Treatment for CTC Obtained by In Vitro Separation

In the method of the present invention, a key step is the resuscitation treatment of CTC obtained by in vitro separation.

A representative method is to resuscitate the isolated CTCs with supernatant cultures of tumor cell cultures.

In the present invention, the time for the resuscitation treatment is not particularly limited, but is usually 2 to 72 hours, preferably 4 to 48 hours, more preferably 12 to 36 hours.

In another preferred embodiment, in the resuscitation process, a conditioned medium of lung fibroblasts may be selected.

In another preferred embodiment, a basal medium to which growth factors have been added may be selected in the resuscitation process. Representative cytokines include, but are not limited to, epidermal growth factor (EGF), basic fibroblast growth factor (basic FGF), or combinations thereof. In general, the concentration of each growth factor is 5-100 ng/ml, and more preferably 10-50 ng/ml.

A representative artificially configured resuscitation medium is a nutrient solution, which is composed of cell culture RPMI-1640, epidermal growth factor (EGF, 20 ng/ml), fibroblast growth factor (basic FGF, 20 ng/ml) and supplement B-27 (purchased from Life Technologies) (1:50 dilution).

Starvation Treatment for CTC

In a preferred method of the present invention, starvation treatment is preferably performed on the resuscitated CTC cells.

Although starvation treatment may not be necessary for certain CTC cells, studies of the present invention have found that starvation treatment contributes to improve the accuracy of detection for the vast majority (or possibly all) of CTC cells.

In the present invention, when starvation treatment is performed, the isolated CTC cells are preferably incubated for a period of time under low glucose concentration or glucose-free culture conditions.

In the present invention, the culturing time of the starvation treatment is usually 1 to 60 minutes, preferably 2 to 30 minutes, more preferably 5 to 20 minutes.

In addition, the low glucose concentration means that the glucose concentration M1 during the starvation treatment is much lower than the glucose concentration M0 under the normal culture conditions of the CTC cells (or their corresponding tumor cells), usually $M1/M0 \leq 1/2$, preferably $\leq 1/5$, more preferably $\leq 1/10$.

In the present invention, when the starvation treatment is performed, the glucose concentration M1 is much lower than 1/50 or less of the glucose concentration M0 under normal culture conditions of the CTC cells (or their corresponding tumor cells) ($M1/M0 \leq 1/50$, preferably $<1/100$), it can be considered to be cultured under glucose-free culture conditions.

The results of the present invention show that after starvation treatment, isolated CTC cells have more consistent and comparable absorption for glucose analogs (e.g., 2-NBDG), thereby making the test results more reliable.

Other Treatment

The study of the present invention has shown that, 2-NBDG will not be ingested by apoptotic cells, while 2-NBDG will be ingested by living cells, and the more malignant the tumor cells are, the faster and more 2-NBDG they will ingest.

However, for the dead cells, the surface of cytomembrane is generally damaged. The fluorescent 2-NBDG diffuses in, resulting in fluorescence occurs. Therefore, the closure for dead cells in advance is more important, and non-specific adsorption of 2-NBDG into dead cells can be avoided, thereby improving detection sensitivity and accuracy.

Therefore, in the present invention, in another preferred embodiment, the resuscitation treatment further comprises the addition of bovine serum albumin for blocking cells and microwell chips to eliminate non-specific adsorption of 2-NBDG.

In another preferred embodiment, the resuscitation process further comprises the addition of a fluorescently modified antibody (such as anti-CD45-FITC) against leukocyte surface antigens to recognize leukocytes, thereby distinguishing CTCs from leukocytes.

In another preferred embodiment, in the resuscitation process, a dead cell dye (eg, EthD-1, ethidium homodimer-1) is added to identify dead cells.

Detection Device for Metabolic Activity of Circulating Tumor Cells

The present invention also provides a device for detecting metabolic activity of circulating tumor cells.

Typically, the device of the invention comprises:
 (a) a "fishbone" chip for capturing CTC;
 (b) a microporous array chip;
 (c) a first container, and a glucose analogue with a detectable label in the first container (e.g., 2-NBDG);
 (d) optional magnetic beads for the capture of circulating tumor cells, wherein the magnetic beads are loaded with antibodies that can specifically bind to the tumor surface antigen; and
 (e) an optional magnetic field device, comprising a permanent magnet or an electromagnet.

In another preferred embodiment, the device further comprises one or more components selected from a group consisting of:
 (f) a second container, and a blocking agent (such as bovine serum albumin) in the second container;
 (g) a third container, and an antibody within the third container for discriminating circulating tumor cells from leukocytes, such as a fluorescently modified antibody against a leukocyte surface antigen (e.g., anti-CD45-FITC)
 (h) a fourth container, and a dead cell dye (e.g., EthD-1, ethidium homodimer-1) in the fourth container for identifying dead cells.

Detection Method for Rare Tumor Cells

The present invention provides a method for detecting rare tumor cells in blood or pleural fluid samples. Typically, it comprises the following steps:
 a. Removing red blood cells from a peripheral blood or a pleural fluid sample by selective lysis;
 b. Co-incubating the remaining cells obtained in the previous step with the fluorescently labeled CD45 antibody to allow the leukocyte surface labeled with a CD45 fluorescent antibody;
 c. Placing the cells processed in the previous step in a microwell array chip, where each microwell can address and accommodate at most one cell, so that each cell on the chip has a unique coordinate position;
 d. Treating the cells in a microwell array with fluorescently labeled glucose analogs;
 e. Detecting glucose uptake and fluorescent signals for CD45 expression for all cells in the microwells by a high-speed fluorescence imaging system; and
 f. Identifying the cells that are of high glucose-uptake and do not express CD45 as active tumor cells and recording the coordinates of the cells.

For a better understanding of the present invention, the inventors provide the following mechanism for reference. However, it should be understood that the scope of protection defined by the claims of the present invention is not limited by this mechanism.

Studies have shown that tumor cell metabolism is characterized by the replacement of oxidative phosphorylation of normal tissue cells with high levels of aerobic glycolysis. Due to the low efficiency of glycolysis, tumor cells need to ingest large amounts of glucose. In the present invention, rare tumor cells in blood or pleural fluid samples are identified based on the biological principle that the ability of tumor cells to ingest glucose is much higher than that of normal cells. In order to increase the specificity of the identification, the leukocyte surface marker CD45 and the necrotic cell dye EthD-1 are further used in the present invention to exclude leukocytes and necrotic cells. Since the detection based on glucose uptake is very simple, a very large number of cells can be identified within a short period of time with the help of a high-speed fluorescence imaging apparatus, and therefore, complicated enrichment of rare tumor cells in blood or pleural fluid samples is not necessary for the present invention as has been reported previously. For pleural effusion samples, they can be detected without enrichment of tumor cells due to a small total number of cells. For blood samples, it is possible to reduce the number of cells by a magnetic ball negative selection of simply labeled CD45 antibodies after lysing red blood cells, and then test can be performed. If the blood sample is smaller or the number of CTCs is high, it can directly be detected without the negative selection.

There are similarities between the method described in the present invention and the tumor imaging detection method which has been used clinically by a radioactive glucose analogue ($^{18}$F-FDG, 2-Fluorine-18-Fluoro-2-deeoxy-D-glucose) for the detection of the tissues for glucose uptake. 18F-FDG is transported by glucose transporter into the cell and phosphorylated by hexokinase to produce 6-PO4-$^{18}$F-FDG and accumulated in cells and can be detected by Positron Emission computed Tomography (PET). Therefore, PET imaging based on radioactive glucose analogue $^{18}$F-FDG can be used to display the location, shape, size, quantity of tumors and radioactivity distribution in tumors. It is mainly used clinically for the diagnosis of malignant tumors and differential diagnosis of benign and malignant tumors, clinical stages, efficacy evaluation, and monitoring of recurrence. Most benign lesions do not ingest or lightly ingest $^{18}$F-FDG. SUV (standard uptake value), the semi-quantitative treatment is clinically used to measure the amount of $^{18}$F-FDG taken by lesions and identify the benign and malignant tissue, generally, SUV>2.5 is considered as the malignant tumor, SUV<2.0 can be considered as benign lesions.

In the case of tumor cells, they have a variety of different phenotypes, genetic characteristics, and metabolic behaviors. In the present invention, the glucose uptake capacity of free tumor cells in blood or pleural fluid is detected. The present inventors' studies have shown that although the glucose uptake capacity of these free tumor cells is one of their metabolic activities, it is closely related to their activity and malignancy degree. Compared with other molecular characteristics, it can more simply and reasonably reflect the vitality and malignancy degree of tumor cells.

In the method of the present invention, in order to ensure the activity of the tumor cells to detect more accurate glucose uptake behavior, fresh blood or pleural fluid samples are needed for detection, and if possible, only red blood cells are lysed without further enrichment. Then, glucose uptake and cell surface CD45 expression were measured directly. If enrichment is necessary due to an excessive number of cells, negative selection using a magnetic ball labeled with a CD45 antibody can generally remove 90 to 99% of the leukocytes, thereby reducing the number of cells by 10 to 100 times. After leukocytes are removed by the leukocyte negative selection method as described above, the recovery rate of tumor cells is usually 97 to 99%, but in the present application, it is preferable not to perform enrichment.

Detection Kit for Rare Tumor Cell

The present invention also provides a kit for detecting rare tumor cells in blood or pleural fluid samples.

Typically, the kit of the invention comprises:
(a) a microwell array chip, wherein each microwell used for containing cells can be addressed;
(b) a fluorescent-labeled CD45 antibody, used to label leukocytes in the sample;
(c) a fluorescent-labeled glucose analog, 2-NBDG, used for detecting glucose uptake capacity of cells in a sample;
(d) a dead cell dye EthD-1, used to label necrotic cells in a sample.

Wherein preferably, the microwell size of the microwell array chip is 15-30 microns, preferably 18-25 microns, so that one microwell can only accommodate one tumor cell. The number of cells (nucleated cells, including leukocytes and tumor cells) is generally 1 to 3 times the number of microwells, for example, a commonly used microwell array chip has 50,000 to 500,000 holes, preferably 150,000 to 250,000 holes.

The main advantages of the present invention comprise:
(a) The method of the present invention can detect and functionally type the glucose uptake capacity of a very small number of CTCs at a low cost, quickly, and accurately. The method of the invention not only can count active CTCs, but also can identify CTCs with high activity and malignancy, and provide a basis for a further molecular detection of these CTCs.
(b) The present invention ensures that a very small number of CTCs are not lost during the whole metabolic activity detection process through the micro-control array chip and magnetic field manipulation, which is the bottleneck of detection of rare cells.
(c) The present invention provides a means of characterizing CTC functions. The importance of CTC is that it not only represents the in situ tumor lesions, but also a direct source of metastasis of tumor blood, while CTC itself has a huge functional heterogeneity, even though these CTCs have similar genomic features. Direct functional characterization of CTCs contributes to understand the status of primary tumors and to assess the metastatic potential of CTCs. The present invention provides a simple, inexpensive, and reliable characterization of the metabolic activity of CTCs, and the metabolic activity typing of CTCs is performed to facilitate the counting of CTCs with high metabolic activity and further molecular tests such as genomes, epigenome detection are performed.
d) The method of the present invention can identify active tumor cells in a large number of cells at low cost, quickly, and accurately. Because the identification method is simple and can be combined with a high-speed fluorescence imaging system, a large number of cells can be rapidly screened, making it possible to directly identify rare tumor cells without enrichment in complex samples. Conventional methods for enrichment of rare tumor cells are complicated to operate and lose a large number of tumor cells, and the method of the present invention abandons the traditional method of detecting the rarest tumor cells in blood or pleural effusion after enrichment, all the cells are contained through a large number of addressable microwells and rare tumor cells are rapidly identified from a very large number of cells through the rapid and simple fluorescence labeling methods and high-speed fluorescence imaging, the entire operation is simple and rapid, and there is little loss of tumor cells due to lack of enrichment. In addition, the method of the present invention directly identifies highly active and malignant tumor cells, which provides a good basis for further molecular detection such as sequencing.

(e) The present invention detects metabolic activity of a tumor cell, that is, glucose uptake ability, so as to quickly and efficiently identify active tumor cells, and is a function-based method for identifying tumor cells from blood or pleural effusion. The obtained active tumor cells are very favorable for subsequent molecular analysis and in vitro culture. The high glucose uptake capacity of tumor cells and the lack of expression of CD45 are common features for tumor cells, without depending on the size of tumor cells, surface antigen expression, etc., and therefore it is a simple and reliable method for tumor cell identification. The method of the present invention allows all cells to be in an addressable location by a microwell array chip, and once identified as a tumor cell, it can be removed for further analysis by manual or automated micromanipulation equipment based on the coordinate location of the cell.

(f) The present invention provides a functional characterization means for tumor cells in blood or pleural fluid samples. Studies have shown that free tumor cells in the blood or pleural fluid are detached from the tumor tissue, and there is a large functional heterogeneity, a significant part of which is in an apoptotic state, and a small part of which with high activity and metastatic potential can eventually form metastasis lesions. Direct functional characterization for free cancer cells contributes to assess the metastatic potential of tumor cells, while active tumor cells are able to perform relatively uniform single-cell genome amplification.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions. Unless otherwise indicated, percentages and parts are by weight and parts by weight.

Materials

In the examples, all of the medium, cell lines, antibodies, magnetic bead are commercially available.

Example 1

Detection of Glucose Analogue Uptake for a Very Small Number of Cells

A microwell array PDMS chip was provided, and its structure is shown in FIG. 1.

30 lung cancer cells A549, H1650, and H1975 were obtained respectively, wherein the surface of each cell was combined with immunized magnetic beads, and the cells were suspended in approximately 200 microliters of PBS, respectively and placed in the microwell array PDMS chip (FIG. 1) to ensure each of them enter and fix in the microwells by manipulating the magnetic field.

Figure 2:
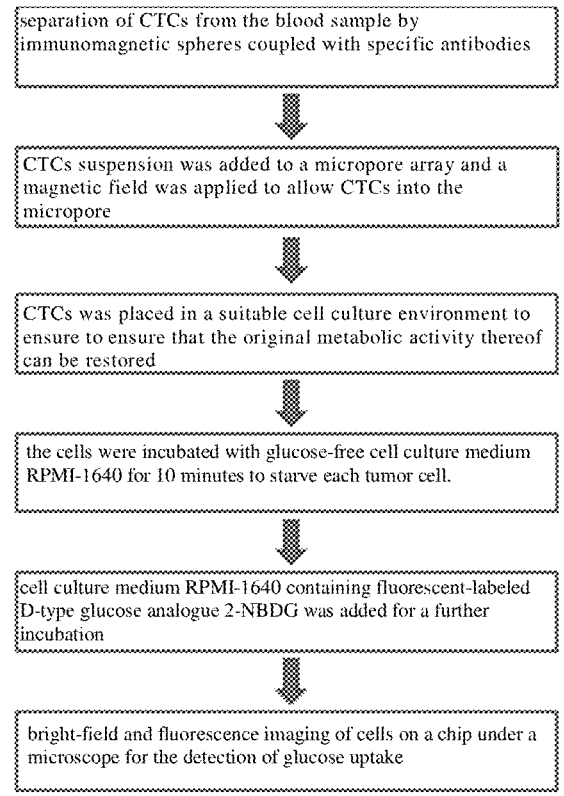
FIG. 2 shows a test flow chart of a method for detecting metabolic activity of circulating tumor cells according to an example of the present invention.

As shown in FIG. 2, the cells were incubated with glucose-free cell culture medium RPMI-1640 for 10 minutes to starve each tumor cell. Then, cell culture medium RPMI-1640 containing 2-NBDG (the concentration was 0.3 mM) was added and the cells were incubated for another 20 minutes. After the incubation, the cells were washed completely and repeatedly with PBS at 4° C. on ice, and the cells were fixed in the microwells by applying a magnetic field. Finally, the cells on the chip were subjected to bright field and fluorescence imaging under a microscope.

Figure 3:
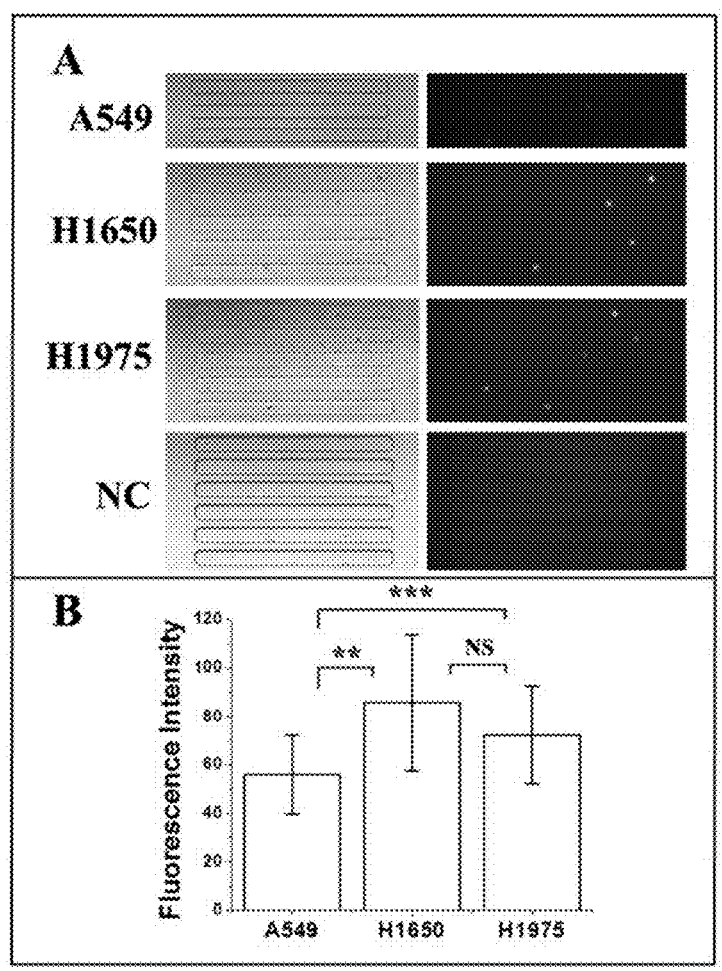
FIG. 3 shows a fluorescence micrograph and the quantification result after the uptake of 2-NBDG by a lung cancer cell line according to one example of the present invention. NC (negative control) is a negative control. The figure shows a fluorescent micrograph after co-incubation of each lung cancer cell line with 2-NBDG for 20 minutes, where the negative control is a fluorescent micrograph after co-incubation of a H1650 cell with 2-NBDG.

The result is shown in FIG. 3. Throughout the testing process, the cells were not lost due to magnetic field constraints. The detection results have showed that H1650 cells with EGFR mutations and H1975 cells show a higher uptake capacity for 2-NBDG glucose analog compared with EGFR wild-type A549 cells, with statistical significance. This test result is basically consistent with the fact that cells with a major oncogene mutation or an anti-oncogene inactivation are often accompanied by upregulation of metabolic pathways, resulting in an increase in metabolic activity.

In addition, the uptake capacity for 2-NBDG glucose analogues in H1650 cells is higher (but not reaching statistically significant levels) compared with H1975 cells. This test result suggests that there is a certain correlation between the higher 2-NBDG glucose analogs in H1650 cells and the inactivation of anti-oncogene PTEN in H1650 cells.

Example 2

Detection of Glucose Analog Uptake of CTC in Peripheral Blood

In this example, the method comprises the following steps:

(1) For 2 ml of peripheral blood samples from lung cancer patients (volunteers), the upper platelet-rich plasma was first removed by low speed centrifugation (200 g) for 5 minutes, and the remaining cells were resuspended in 2 ml with Hank's balanced salt solution (HBSS), and a group of biotin-labeled antibodies (targeted antigens were EpCAM, EGFR, HER2, MUC1, respectively, with a final concentration of 1 μg/mL for each antibody) was added and co-incubated for 1 hour. The excess antibodies were centrifuged (300 g, 5 minutes) and removed, and then streptavidin-labeled magnetic balls (0.8 μm) were added for co-incubation for 30 min, excess magnetic balls were removed by centrifugation (300 g, 5 min), and the cells were resuspended in 5 ml of HBSS to form the pretreated sample.

Figure 4:
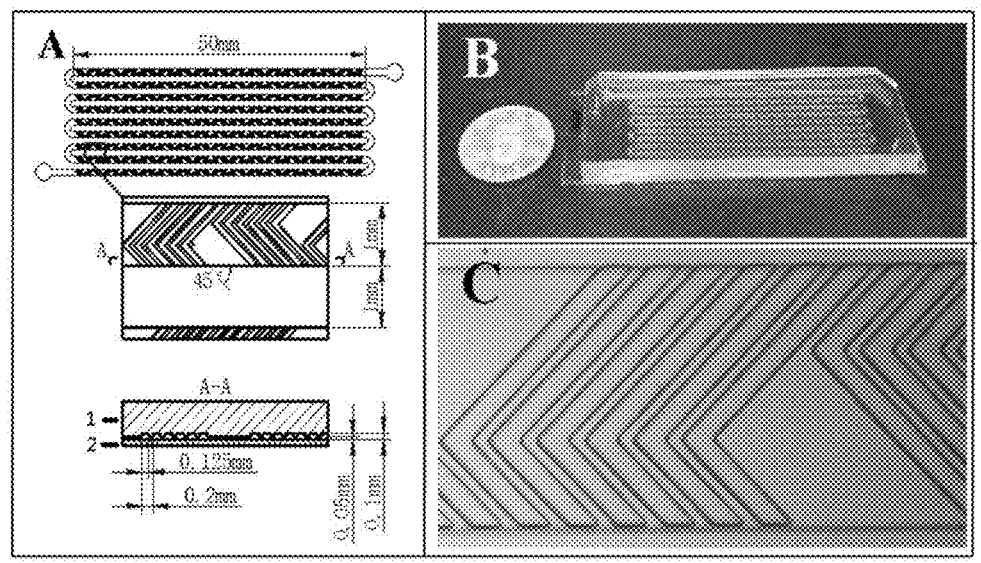

(2) A fishbone chip was provided, with a structure shown in FIG. 4.

(3) For the microchannels of the fish bone chips, it was blocked with a mixture of 10% goat serum and 3% bovine serum albumin for one hour to avoid non-specific adsorption of cells, and then 5 ml of the above treated cell suspension passed through the chip channel at a flow rate of 5 mL/h through the constant current syringe pump, and an upward magnetic field was set above the chip to achieve dynamic CTC capture during the flow process. After completed, the chip was washed with HBSS at a flow rate of 10 mL/h for 5 minutes to remove non-specifically adsorbed cells, and then the magnetic field was removed to collect the CTCs in about 200 microliters of liquid, wherein in addition to the CTC, a very small number of non-specifically captured leukocyte were also included.

(4) The above-mentioned about 200 microliters of the cell suspension was placed in a microwell array PDMS chip, and the nanopore on the chip was preliminarily incubated with 0.1% of type I collagen at 37° C. for 2 hours to adsorb collagen on the surface. By manipulating the magnetic field, it was ensured that each cell entered and fixed in the microwells.

(5) Artificial preparation of resuscitation medium (cell culture medium RPMI-1640, 20 ng/ml of epidermal growth factor EGF, 20 ng/ml of fibroblast growth factor basic FGF, and 1:50 diluted supplements B-27) were added to the micro-chips, and placed in a 37° C., 3% oxygen concentration of a cell culture incubator for 24 hours, and then incubated in a resuscitation medium supplemented with bovine serum albumin (cell culture medium RPMI-1640, 20 ng/ml of epidermal growth factor EGF, 20 ng/ml of fibroblast growth factor basic FGF, 1:50 dilution of supplement B-27, 1% bovine serum albumin BSA) for 30 minutes to block the chip.

(6) After completion of the CTC culture on the chip, the cells were incubated for 10 minutes with glucose-free cell culture medium RPMI-1640, and then which were starved. Then, a cell culture medium RPMI-1640 containing 2-NBDG (concentration: 0.3 mM) was added, and the cells were incubated for another 20 minutes.

(7) After the incubation was completed, the cells were washed completely and repeatedly with PBS at 4° C. on ice, and a magnetic field was applied to ensure that the cells were fixed in the nanopores.

(8) Bright-field and fluorescence imaging of the cells on the chip was performed under a microscope.

Figure 5:
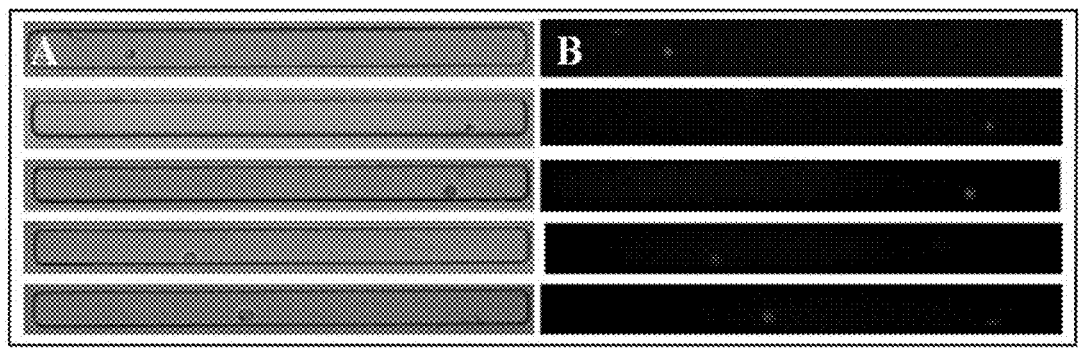

As shown in FIG. 5, a stronger fluorescence signal was detected in 5 CTCs, showing a rapid uptake of 2-NBDG, whereas a fluorescence signal was not detected in leukocytes, i.e., uptake of 2-NBDG. KRAS mutations were detected in these CTCs in subsequent single cell sequencing.

Comparative Example 1

Example 2 was repeated, wherein the peripheral blood sample used was the same batch of peripheral blood samples from the same lung cancer patient (volunteer). The difference is that the on-chip cultivation process of step (5) was omitted, and starvation and 2-NBDG uptake experiments of step (6) were directly performed.

Results: No fluorescence signal from the cells that could be distinguished from the background could be detected, i.e., the growth and proliferation of CTCs that have just been isolated in vitro were inhibited and the metabolic activity was greatly reduced, making it difficult to be detected.

Example 3

Example 2 was repeated, wherein the peripheral blood sample used was the same batch of peripheral blood samples from the same lung cancer patient (volunteer). The difference is that in step (5), the upper conditioned medium in the culture dish of lung cancer cell H1650 and the upper conditioned medium in the lung fibroblast culture dish were combined in a ratio of 1:1 to form a new conditioned medium for CTC culturing in microchip.

As a result, similar results as in Example 2 were obtained, and significant fluorescent signals were detected in 6 CTCs.

Example 4-6

Example 2 was repeated with the following differences:
In Example 4, in the resuscitation treatment, the addition of the blocking agent of bovine serum albumin was also included to block cells and microwell chips, thereby eliminating the non-specific adsorption of 2-NBDG (Example 4);

In Example 5, in the resuscitation process, the addition of a fluorescent-modified antibody (e.g., anti-CD45-FITC) against a leukocyte surface antigen was also included to recognize the leukocyte, thereby distinguishing the CTC from the leukocyte;

In Example 6, in the resuscitation process, a dead cell dye (e.g., EthD-1, ethidium homodimer-1) was added to identify dead cells.

As a result, similar results as in Example 2 were also obtained, significant fluorescence signals were detected in 5, 6 and 5 CTCs in Example 4-6, respectively.

In addition, since the blocking agent of bovine serum albumin, fluorescent-modified antibodies against leukocyte surface antigens, and dead cell dyes were added in these Examples 4-6, it was more convenient to select CTC cells and it was also less likely to confuse CTC cells with irrelevant cells.

Discussion

At present, clinically, the radioactive substances that can be phagocytosed or swallowed by tumor cells and PET imaging of radioactive substances can be used to display the location, shape, size, quantity, and radioactivity distribution in tumors, and are mainly used clinically for the diagnosis of malignant tumors, differential diagnosis of benign and malignant tumors, clinical staging, efficacy evaluation, and monitoring of recurrence.

However, there is a great deal of heterogeneity in tumors. For example, mutations on one side of the tumor are likely to be different from those on the other side. Clinically, the relatively more malignant tissues are usually sampled for sequencing. The CTC also has the same problem. If there are many CTCs, the signals of malignant CTCs may be diluted or submerged when they are mixed and sequenced, or they may not be detected due to insufficient sensitivity. Therefore, selecting simply and efficiently the most representative or highly malignant CTCs from CTC cells is a difficult problem.

In the present invention, the glucose uptake ability of the extremely rare CTCs in the blood was detected based on glucose analogues with fluorescent groups and corresponding methods and devices, so that the metabolic functions of CTCs can be typed, thereby effectively selecting the most representative or highly malignant CTCs.

In the present invention, the glucose uptake of CTC (generally, 1-1000) in the peripheral blood of a very small number of tumor patients was measured, and the principle is to detect the uptake ability of the labeled glucose analogs by the CTC, whereas there are similar metabolic pathways (especially very similar in the intake chain) between the glucose analog and the normal glucose. In addition, the metabolic characteristics of tumor cells are the replacement of oxidative phosphorylation in normal tissue cells with high levels of aerobic glycolysis. Because of the low efficiency of glycolysis, tumor cells need to ingest a large number of glucose.

The present invention mainly includes three aspects of the technical challenges: (1) to ensure that the CTC is not lost when a very small number of CTCs are tested for glucose analogue uptake; (2) The process of enrichment and isolation of CTC from peripheral blood samples from tumor patients needs to ensure that the damage to CTC activity is very small; (3) Since there is a certain damage for CTC during its in vitro isolation process, it is in a state of growth inhibition and low metabolic activity. Therefore, it is necessary to place CTC in an appropriate cell culture environment to restore its original metabolic activity.

In the present invention, the glucose uptake capacity of rare tumor cells is quantitatively detected by labeled glucose analogs, such as the fluorophore-labeled D-glucose analog 2-NBDG, which has a similar metabolic pathway to that of D-glucose, which was entered into cell through the glucose transporter (GLUT) and its C-6 position is then phosphorylated by hexokinase. Studies have shown that 2-NBDG can be rapidly ingested by malignant cells compared with benign cells, and therefore is an optical marker for detecting malignant cells. After a transient glucose "starvation" for rare tumor cells, they were co-incubated with 2-NBDG for a period of time, and washed with iced PBS, and the fluorescence signal emitted from the uptake of 2-NBDG by the cells was detected by fluorescence microscopy.

For the technical challenge 1, that is, when testing a very small number (as few as one) of rare cells, it is necessary to ensure that the cells are not lost during the detection process. Therefore, the method used in the present invention is to separate the CTC from the blood sample by using an immunomagnetic bead coupled with a specific antibody, and then to add the CTC suspension to a microwell array (see FIG. 1) and to apply a magnetic field appropriately so that all CTCs combined with magnetic balls enter microwells under the action of a magnetic field, and the number of microwells (thousands) is much greater than that of CTCs, thereby ensuring that there is no more than one CTC in the microwell, and CTC is confined to microwells by the magnetic field during the detection process and will not be lost due to adding reagents or washing steps.

For technical challenge 2, that is, for the process of enrichment and isolation of CTCs from peripheral blood samples of tumor patients, it is necessary to ensure that the damage to CTC activity is very small. The method of pretreating the blood by red blood cell lysis and density gradient centrifugation has certain damage to other cells and should be avoided. The present invention combines immunomagnetic with microfluidic chip technology to directly separate CTCs from blood without prior removal of red blood cells or leukocyte. However, plasma and some platelets can be removed in advance by low-speed centrifugation, and the remaining cells must be resuspended in a balanced solution containing glucose, such as Hank's Balanced Salt Solution (HBSS) or cell culture medium.

For the technical challenge 3, that is, in vitro isolation process has a certain damage to the CTC, so that it is in a state of growth inhibition and low metabolic activity, and the CTC needs to be placed in an appropriate cell culture environment to ensure that it can restore the original metabolic activity, core of which lies in its ability to effectively mimic the microenvironment of tumors in vivo. This microenvironment may include physical microenvironments such as low oxygen concentration, chemical microenvironments such as various growth factors, supplements, and three-dimensional culture media and so on, and biological microenvironment such as "feeding" cells co-cultivated with CTC or the supernatant containing secretions of "feeding" cells, etc., "feeding" cells herein include tumor cells or fibroblasts with the same origin as the CTC, which may be derived from cell lines or patient tissue samples. In general, there is no unified CTC culture method, and different sources of CTC can adopt different culture methods so as to obtain the best culture effect.

Example 7

Detection of Glucose Analog Uptake in Tumor Cells

Figure 6:
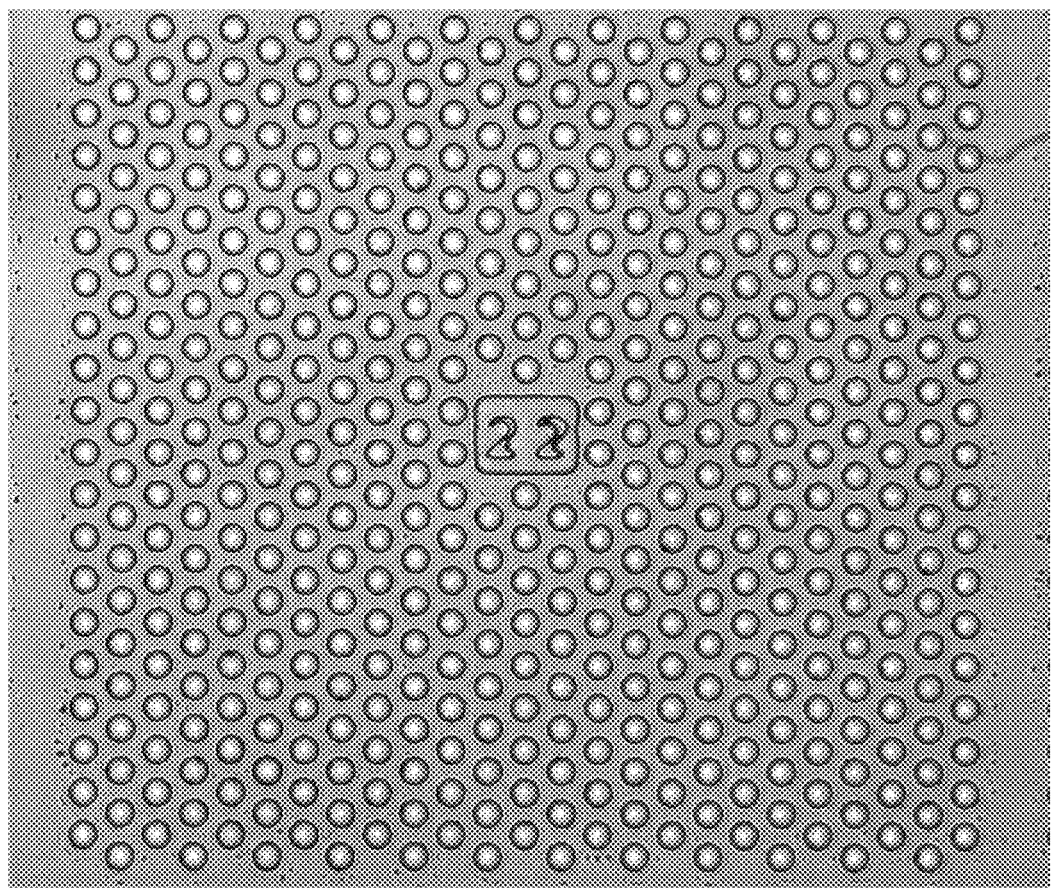
FIG. 6 shows a bright field microscope view of a portion of a microwell array chip according to an example of the present invention. Each microwell of the microwell array chip exhibits 20 micrometers in diameter and 30 micrometers in depth. Each 500 microwells form a small area and is marked with numbers. A typical microwell array chip consists of 400 such small areas labeled with numbers, with a total of 200,000 microwells.

A microwell array PDMS chip was provided, the structure of which is shown in FIG. 6, wherein each microwell has a diameter of 20 μm and a depth of 30 μm. Each 500 microwell forms a small area and is marked with numbers to realize the addressability for each microwell. A typical microwell chip consists of 400 small areas that were digital coded as shown in FIG. 1, with 200,000 microwells in total.

Figure 7:
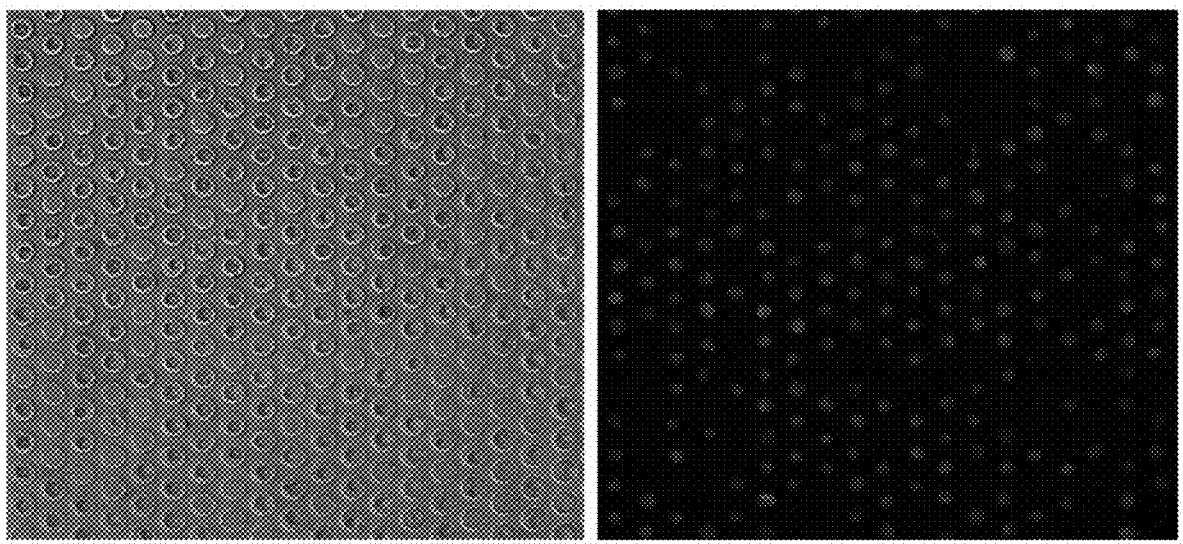
FIG. 7 shows a bright field microscope view of the distribution of cells in the microwells after the suspension containing the lung cancer cell line H1650 cells was added to the microwell array chip, and a fluorescence microscope view after the cells uptake of 2-NBDG. As can be seen from the figure, when the cell concentration is appropriate, there are cells in most of the microwells and there is only at most one tumor cell per microwell, and the cells are located at the center of the microwell. Because the coordinates of each microwell are fixed, the cells in the microwells can be addressed. The cells in the microwells can be removed by manual or automated micromanipulation equipment. The fluorescence-labeled glucose analogue 2-NBDG has an excitation and emission wavelength of 465 nm and 540 nm, and the emitted fluorescence is green when taken into cells, and can be observed using a FITC-based light filter.

The cell suspension of lung cancer cell H1650 was added on a microwell array chip and placed and washed with a glucose-free cell culture medium RPMI-1640. As shown in FIG. 7, most of the microwells had cells and each microwell had only at most one cell, and meanwhile, the cell was in the center of the microwell.

Cells were incubated with glucose-free cell culture RPMI-1640 for 10 minutes and tumor cells in the microwells were starved. Then, cell culture medium RPMI-1640 containing 2-NBDG (concentration: 0.3 mM) was added and the cells were incubated for another 20 minutes. After the incubation was completed, the cells were thoroughly and repeatedly washed with PBS at 4° C. on ice, and finally the cells on the chip were subjected to fluorescence imaging under a microscope, as shown in FIG. 7. The fluorescence-labeled glucose analogue 2-NBDG has an excitation and emission wavelength of 465 nm and 540 nm, and the emitted fluorescence was green after ingestion into the cells, and can be observed using a FITC-based filter.

Example 8

Detection of Tumor Cells in Pleural Fluid Samples from Lung Cancer Patients

Figure 8:
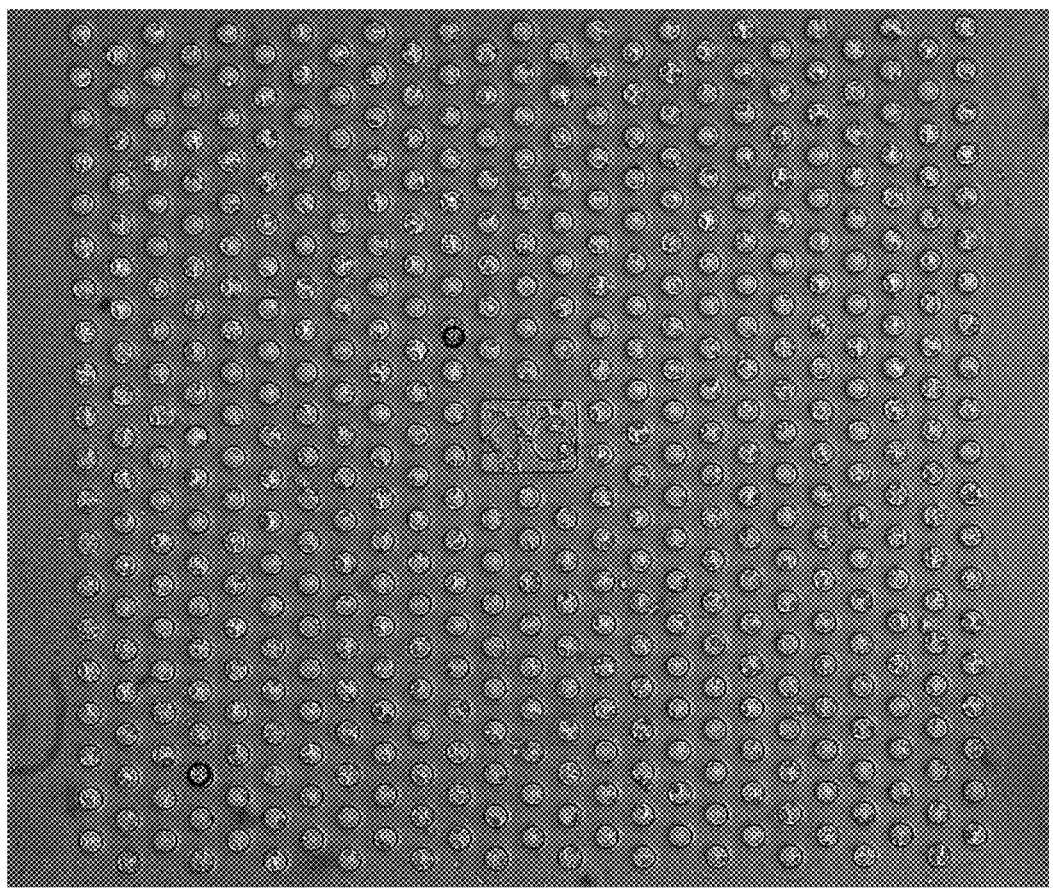
FIG. 8 shows that in an example of the present invention, after pleural fluid samples from patients with lung cancer undergo erythrocyte lysis, the remaining cells are centrifuged and resuspended, and then added to the microwell array chip. The cells are almost in the well, but due to the small size of some white blood cells, there are more than one cells in the part of the microwell.

In this example, the method includes the following steps:
(1) After filtering 40 ml of the pleural effusion from lung cancer patients with 150 mesh gauze, the cells were separated by centrifugation (500 g, 5 minutes), 5 ml of red cell lysate (BD) was added and lysed in darkness for 5 minutes, centrifuged again (500 g, 5 minutes), the supernatant was discarded, the cells were resuspended and washed with Hank's balanced salt solution (HBSS), centrifuged (500 g, 5 minutes), the supernatant was discarded, and 2 ml of HBSS was added to resuspend cells;
(2) After counting, 500 μl of cell suspension (approximately 1 million cells) was taken and 2 μl of APC-labeled CD45 antibody was added and incubated for 1 hour on inverter.
(3) Centrifugation, the supernatant was discarded and the cells were diluted with HBSS, the cell suspension was added dropwise on two microwell array chips (each chip contains 200,000 microwells) and allowed to stand for 10 minutes;
(4) The chip surface solution was removed, 100 microliters of glucose-free DMEM cell culture medium was added on each chip, and the cells were starved for 10 minutes. The microscopic bright-field image of the chip is shown in FIG. 8. The cells were basically in the microwells. However, due to the small size of some leukocyte, there are more than one cells in some microwells;
(5) The solution on chip surface was removed, fluorescent-labeled glucose analogue 2-NBDG (400 μM) and cell necrosis fluorescent dye EthD-1 (4 μM) were added on each chip, and placed in a 37° C. incubator for 20 min;
(6) After incubation, the chips were washed with ice PBS for 8 times and imaged with a high speed fluorescence imaging device.

Figure 9:
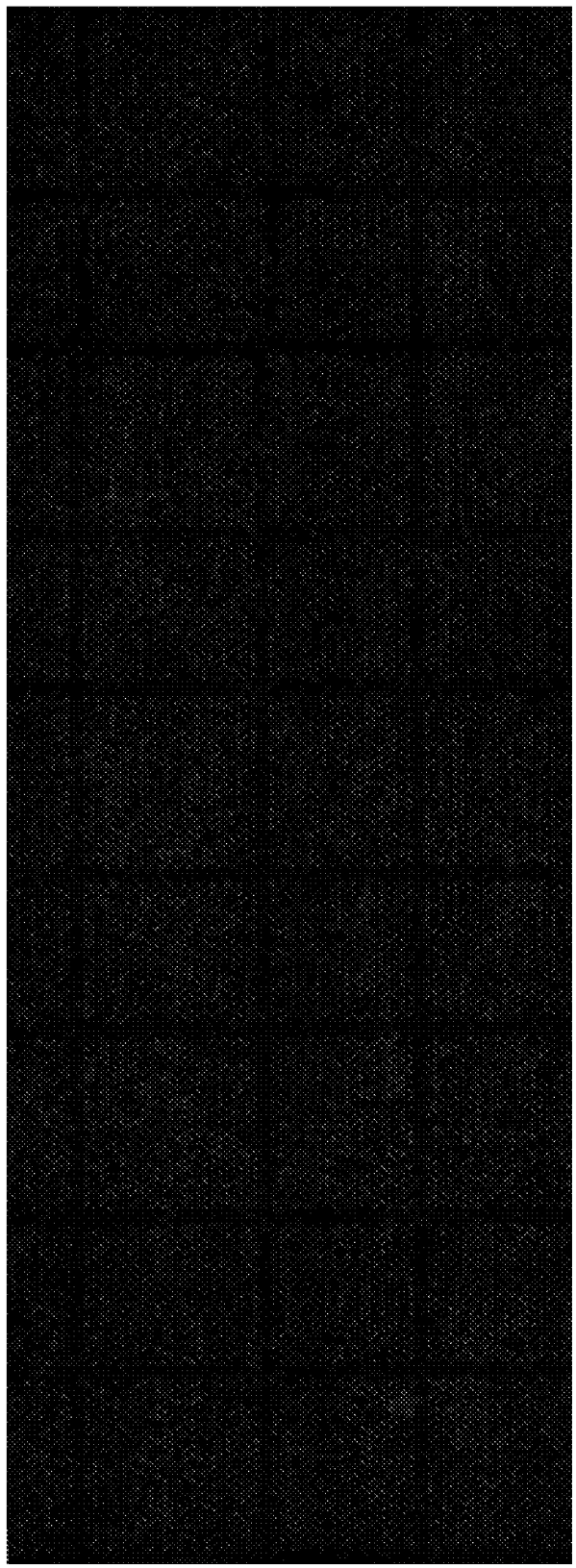
FIG. 9 shows a fluorescence field view of a microwell array chip scanned using a high-speed fluorescence imaging device, showing a portion of a microwell array chip in which the nuclei of cells in the microwells were stained via DAPI.

FIG. 9 showed a fluorescence field view of a microwell array chip scanned using a high-speed fluorescence imaging device, showing a portion of a microwell array chip in which the nucleus of cells in the microwells were stained with DAPI. The high-speed fluorescence imaging device can quickly image the 2-NBDG (green), CD45 (red), and EthD-1 (yellow) fluorescence fields on the chip, and screen 2-NBDG strongly positive, CD45 negative, and EthD-1-negative cells through the procedure, which were identified as suspected tumor cells and their coordinate positions were recorded.

Figure 10:
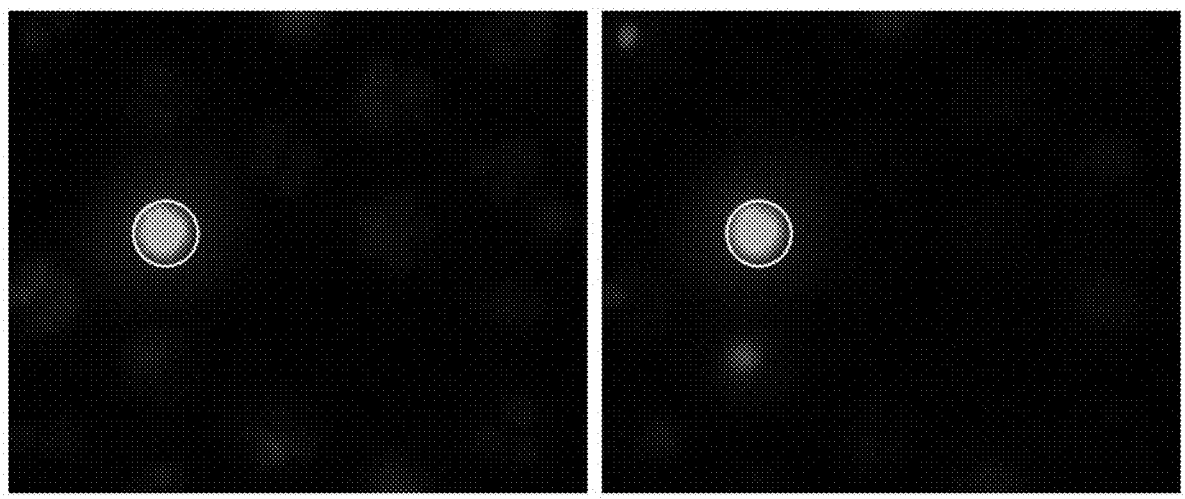
FIG. 10 shows that in an example of the present invention, a fluorescence microscopic view of a pleural fluid sample from a lung cancer patient after erythrocyte lysing and after the remaining cells have been co-labeled with CD45-Allophycocyanin (APC) antibody, 2-NBDG, and EthD-1, wherein the left side is the coincidence pattern of CD45-APC (red) and 2-NBDG (green), the right side is the coincidence pattern of 2-NBDG (green) and EthD-1 (yellow), and the cells marked red are CD45 positive cells, i.e., the leukocytes, the cells marked green are cells ingesting 2-NBDG, and the cells marked yellow are necrotic cells. This figure clearly shows a cell that is CD45 negative (without expression of leukocyte markers), 2-NBDG strongly positive (high glucose uptake) and EthD-1 negative (live cells), and is significantly larger in size than surrounding leukocytes, so that the cells are more likely to be tumor cells that are free from pleural effusion.

The results were shown in FIG. 10. The left side showed a coincidence pattern of CD45-APC (red) and 2-NBDG (green), and the right side showed a coincidence pattern of 2-NBDG (green) and EthD-1 (yellow) and the cells marked with red were CD45-positive cells, i.e., leukocytes, the cells marked with green were cells that ingested 2-NBDG, and the the cells marked with yellow were cells that had already necrosed. A cell that is CD45 negative (without expression of leukocyte markers), 2-NBDG strongly positive (high glucose uptake), and EthD-1 negative (live cells), and is significantly larger in size than surrounding leukocytes was clearly shown in this figure, so that the cell is more likely to be a tumor cell that is free from pleural effusion.

Figure 11:
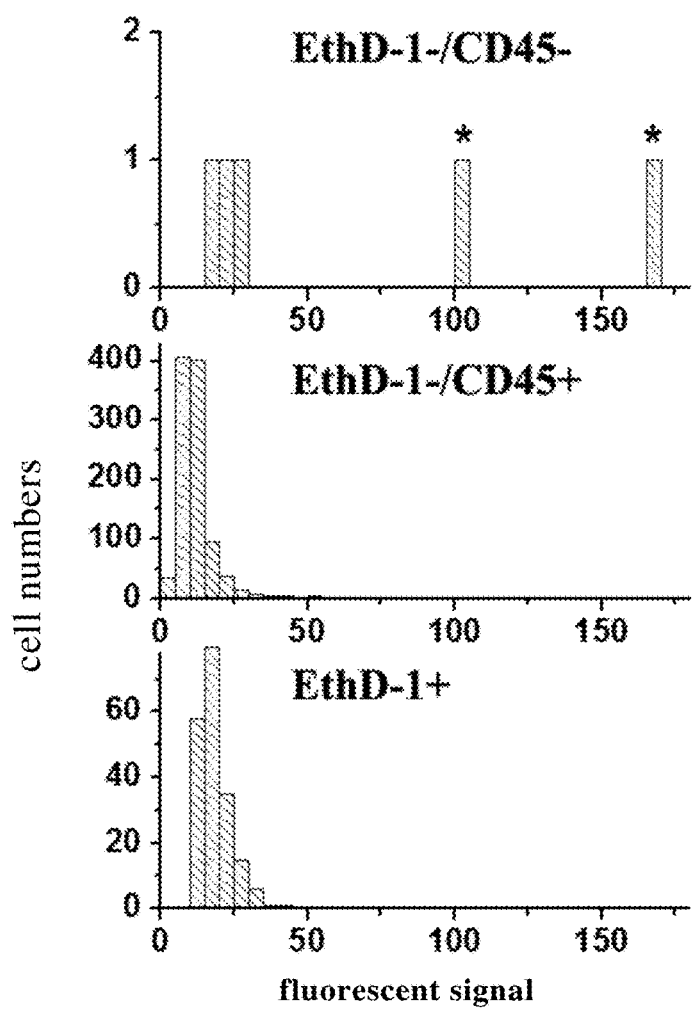
FIG. 11 shows statistics of 2-NBDG uptake by all cells in a small area containing 500 microwells. The lower panel is a fluorescence signal distribution for all EthD-1 negative, i.e., 2-NBDG uptake by necrotic cells. The middle panel is a fluorescence signal distribution for all CD45 positive and EthD-1 negative, i.e., 2-NBDG uptake by live leukocytes. Whereas the upper panel is a fluorescence signal distribution for all CD45 negative and EthD-1 negative cells uptaking 2-NBDG, wherein there are two strongly 2-NBDG-positive cells, i.e., cells with high glucose uptake, one of which is shown in FIG. 10.

FIG. 11 showed statistics of 2-NBDG uptake by all cells in a small area containing 500 microwells. The lower panel was a fluorescence signal distribution for all EthD-1 negative, i.e., 2-NBDG uptake by necrotic cells. The middle panel was a fluorescence signal distribution for all CD45 positive and EthD-1 negative, i.e., 2-NBDG uptaken by the live leukocytes. Whereas the upper panel was a fluorescence signal distribution for all CD45 negative and EthD-1 negative cells uptaking 2-NBDG, wherein there were two strongly 2-NBDG-positive cells, i.e., cells with high glucose uptake, one of which was shown in FIG. 10.

Figure 12:
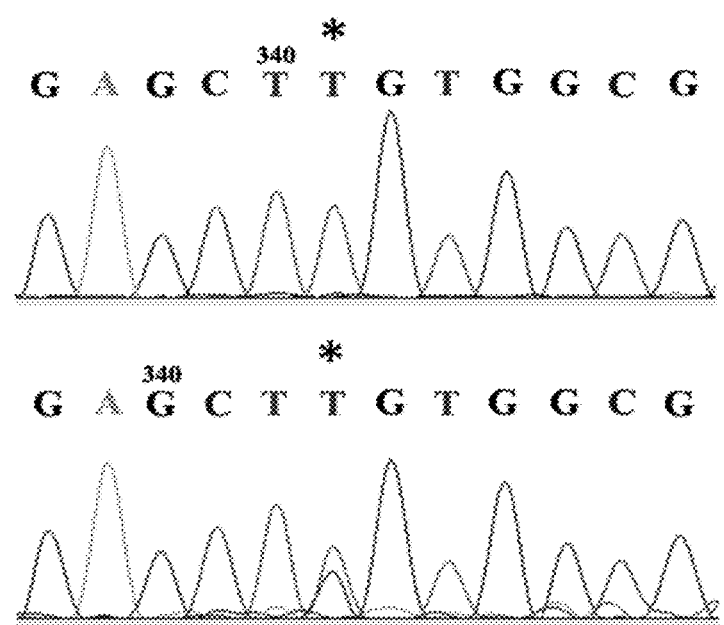
FIG. 12 shows the single cell taken out from the suspected tumor cells shown in FIG. 11 by micromanipulation equipment, cell lysis, DNA extraction and single cell genome amplification, PCR against second exon of the oncogene KRAS, and sequencing, demonstrating that the G12C mutation was present in the second exon of KRAS in these two cells. The position of the * in the figure is the mutation position, and it is changed from G to T. This mutation is consistent with that in the patient's tissue and it can be confirmed that both cells are tumor cells.

FIG. 12 showed the single cell was taken out from the suspected tumor cells shown in FIG. 11 by micromanipulation equipment, cell lysis, DNA extraction and single cell genome amplification, PCR against second exon of the oncogene KRAS, and sequencing, demonstrating that the G12C mutation was present in the second exon of KRAS in these two cells. The position of the * in the figure was the mutation position, and it was changed from G to T. This mutation was consistent with that in the patient's tissue and it can be confirmed that both cells were tumor cells, demonstrating that a rapid identification method based on glucose uptake and CD45 expression is effective. In this sample, a total of four suspected tumor cells (including the two shown in FIG. 11 and FIG. 12) were taken out and all were sequenced as tumor cells, indicating that this method is accurate and reliable for identifying tumor cells.

In addition, in addition to the four tumor cells which were taken out by the micromanipulation device for single cell sequencing, the other six tumor cells in the microwell for the same sample were fixed, permeable membrane, and CK/DAPI immunofluorescent staining (note: CD45 had been stained). The results showed that only 3 of the 6 tumor cells were positive for CK, and the remaining 3 tumor cells were negative for CK, indicating that the identification of CTC based on CK/CD45/DAPI immunofluorescence staining method was not reliable.

Example 9

Detection of Glucose Analog Uptake in Tumor Cells in Peripheral Blood Samples from Patients with Lung Cancer In this example, the method includes the following steps:
(1) 1 ml of peripheral blood samples from lung cancer patients were centrifuged at low speed (200 g, 5 minutes) to remove the upper platelet-rich plasma, and the remaining cells were re-suspended with HBSS, and red blood cell lysate (BD company) was added for lysis in darkness for 5 minutes, centrifuged again (500 g, 5 minutes), the supernatant was discarded and the cells were re-suspended and washed with Hank's Balanced Salt Solution (HBSS), centrifuged (500 g, 5 min), the supernatant was discarded and 2 ml of HBSS was added to re-suspend cells;
(2) After counting, according to the cell number of 1:20, the magnetic ball labeled with CD45 antibody (Stemcell) was added and the cells were subjected to incubation on the inverter. After 15 minutes, 4 microliters of APC-labeled CD45 antibody was added and the cells were subjected to incubation for another 45 minutes;
(3) The cell suspension was transferred to a centrifuge tube, and the magnetic pole (Stemcell) was inserted and placed for 10 minutes. The leukocytes on the surface, of which the magnetic balls of the CD45 antibody were bound, were adsorbed on the wall of the centrifuge tube, and the liquid in the tube was transferred to 1.5 ml of EP tube. In the tube, it contained cells that did not have CD45 antibody-bound magnetic balls on their surfaces, negative selection of this step would remove 90-99% of leukocytes;
(4) Centrifugation, the supernatant was discarded, and the cells were diluted with HBSS, and the cell suspension was added dropwise on one microwell array chip (each chip contained 200,000 microwells) and placed for 10 minutes;
(5) the solution on chip surface was removed and 100 microliters of glucose-free DMEM cell culture medium was added on each chip, and the cells were starved for 10 minutes. The microscopic bright-field images of the chip were shown in FIG. 8. The cells were basically in the microwells. However, due to the small size of some leukocytes, there are more than one cells in some microwells;
(6) the solution on chip surface was removed and fluorescent-labeled glucose analog 2-NBDG (400 μM) and necrosis fluorescent dye EthD-1 (4 μM) were added on each chip and placed in a 37° C. incubator for 20 min;
(7) After the incubation was completed, the chip was washed with ice PBS for 8 times and imaged with a high-speed fluorescence imaging apparatus.

Figure 13:
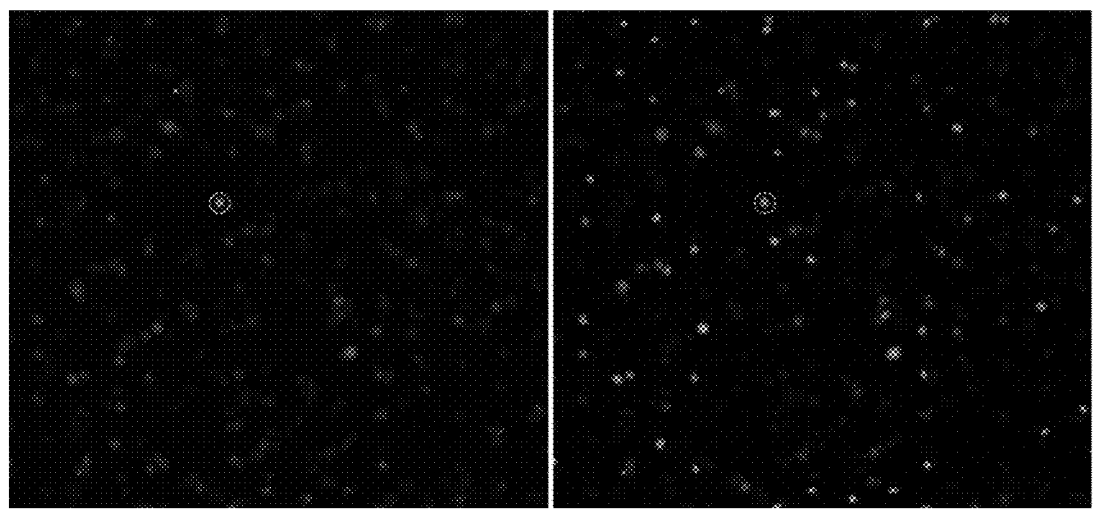
FIG. 13 shows a fluorescence microscopic field view of an example of the present invention in which a whole blood sample from a lung cancer patient is lysed by a red blood cell, and then the remaining cells are co-labeled with CD45-APC, 2-NBDG, and EthD-1. Wherein the left side is the coincidence pattern of CD45-APC (red) and 2-NBDG (green), the right side is the coincidence pattern of 2-NBDG (green) and EthD-1 (yellow), and the cells marked red are CD45 positive cells, i.e., the leukocytes, the cells marked green are cells ingesting 2-NBDG, and the cells marked yellow are necrotic cells. A CD45-negative (without expression of leukocyte marker), 2-NBDG strongly positive (high glucose uptake) and EthD-1 negative (live cell) cell is clearly shown in the figure, and it is more likely to be a circulating tumor cell.

FIG. 13 showed a small area containing 500 microwells, the left side was the coincidence pattern of CD45-APC (red) and 2-NBDG (green), the right side was the coincidence pattern of 2-NBDG (green) and EthD-1 (yellow), and the cells marked as red were CD45 positive cells, i.e., the leukocytes, the cells marked as green were cells ingesting 2-NBDG, and the cells marked as yellow were necrotic cells. A CD45-negative (without expression of leukocyte marker), 2-NBDG strongly positive (high glucose uptake) and EthD-1 negative (live cell) cell was clearly shown in the figure, it was more likely to be a circulating tumor cell.

Figures 14, 15:
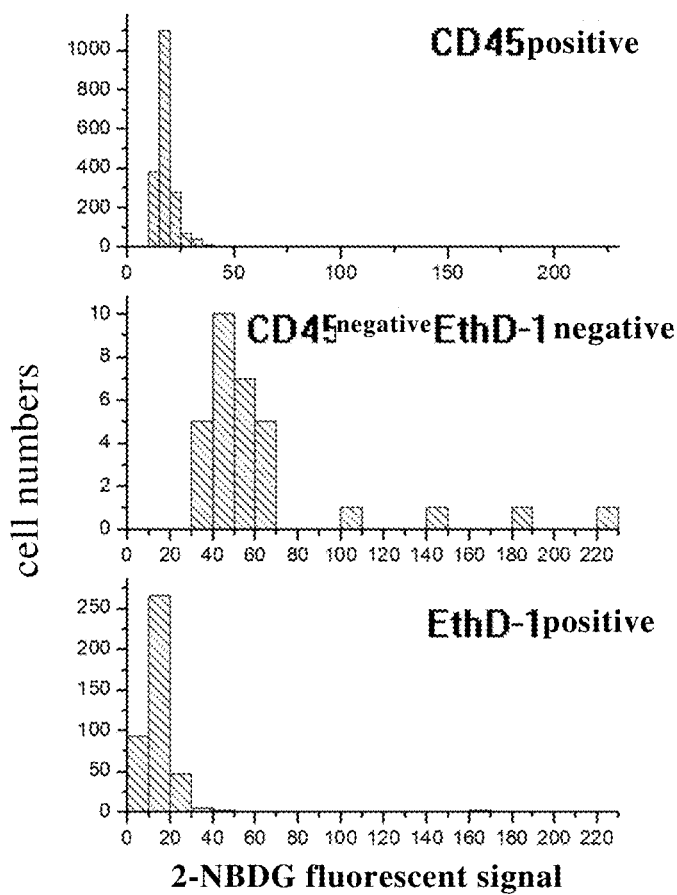
FIG. 14 shows some of the statistical results in the sample of FIG. 12, where the upper panel shows a fluorescence signal distribution of 2-NBDG uptaken by all CD45 positive cells and the middle panel shows a fluorescence signal distribution of 2-NBDG uptaken by all CD45 negative and EthD-1 negative cells, while the bottom panel shows a fluorescence signal distribution of 2-NBDG uptaken by all EthD-1 negative, i.e., necrotic cells. Wherein four of these cells were CD45-negative, EthD-1 negative and 2-NBDG strongly positive, and after sequenced, it was found that the gene mutation feature EGFR L858R is consistent with that in the tumor tissue of the patients and is identified as a tumor cell.
FIG. 15 shows the capture efficiency of two representative CTC capture techniques in the human peripheral blood, one of which is a staggered fishbone chip with surface-modified antibodies, and the other is French Rarecells system based on the filter membrane ISET technology. The capture efficiency is obtained by enriching, selecting and counting tumor cells of previously fluorescently labeled 50 different cell lines that were accurately added in one milliliter of healthy human blood.

FIG. 14 showed some of the statistical results for the sample of FIG. 13 (approximately 2000 cells), wherein the upper panel shows a fluorescence signal distribution of 2-NBDG uptaken by all CD45 positive cells and the bottom panel shows a fluorescence signal distribution of 2-NBDG uptaken by all EthD-1 negative, i.e., necrotic cells, the middle panel shows a fluorescence signal distribution of 2-NBDG uptaken by all CD45 negative and EthD-1 negative cells, wherein the four suspected tumor cells whose 2-NBDG uptake fluorescence signal was greater than 100, were subjected to the single cell genome sequencing after being removed through the micromanipulation device. It was found that the gene mutation characteristic EGFR L858R was identical to the tumor tissue and was indeed a tumor cell, indicating that a rapid identification method based on glucose uptake and CD45 expression is effective.

Comparative Example 2

Capture Rate of CTC Enrichment Method

Two representative CTC enrichment assays in human peripheral blood were selected, one of them was an interlace fishbone chip with surface-modified capture antibodies (see Stott S L, et al. Proc. Natl. Acad. Sci. (USA 2010, 107, 18392), and the other was the commercial French Rarecells system based on the ISET technology of filter membranes (with a pore size of 8 micron). Since it is impossible to know the true number of CTCs in a patient sample, the capture efficiency of the enrichment technique is generally estimated by accurately adding 100 tumor cell lineage cells to one milliliter of healthy human blood sample and then being counted by enrichment and sorting. Because different cells had different sizes and different surface antigen expressions, 6 different tumor cell lines were used in this experiment for the simulation experiments to calculate the capture efficiency of different methods. Among them, antibody-based capture methods selected the corresponding specific antibodies according to the expression levels of surface antigens of different cell lines. FIG. 15 showed the evaluation on the enrichment effect of two different techniques on five tumor cell lines. There was no doubt that the enrichment steps had resulted in the loss of the CTC. Among them, the ISET technology based on the 8 micron pore size of filter membrane has a poor effect on the enrichment for small-size tumor cells. At the same time, tens of thousands of leukocytes were specifically mixed in this method, and the CTC was stuck in the microwells and difficult to be removed. The antibody-based microfluidic chip capture technique was not effective for the enrichment of cell lines with low expression of antigens such as EpCAM. Even if multiple antibodies against different antigens were used, it is usually difficult to achieve good effects. The same CTCs were immobilized on the chip, and it was difficult to be removed for further analysis, and thousands of leukocytes were specifically mixed in this method. Therefore, the current CTC enrichment detection technology would lose CTCs in the enrichment step, and it was difficult to predict the number of losses. However, the CTC identification step cannot accurately and reliably identify tumor cells and the identified CTCs cannot be subjected to further sequencing to find the targets of targeted drug due to the immobilization to nuclear staining, while the above enrichment method is difficult to accurately and reliably remove CTCs for further analysis.

Discussion

The joint detection of glucose uptake and leukocyte marker CD45 in peripheral blood or pleural fluid samples of tumor patients was performed in the present invention, thereby rapidly identifying the tumor cells in which the number of the free cells is extremely rare, the principle of which is that active tumor cells can rapidly ingest the fluorescent-labeled glucose analogs, and the glucose analogs have a similar metabolic pathway as normal glucose (especially in the intake phase). At the same time, tumor cells do not express the leukocyte marker CD45. This method is a universal feature of tumor cells, without depending on the size of tumor cells, surface antigen expression, etc., and therefore is a simple and reliable method for tumor cell identification.

The fluorescent-labeled glucose analog used in the present invention is 2-NBDG, which has a similar metabolic pathway as D-type glucose, enters the cell via glucose transporter (GLUT), and then its C-6 position is phosphorylated by hexokinase. Studies have shown that 2-NBDG can be rapidly ingested by malignant tumor cells compared to benign cells, and therefore it is an optical marker for detecting malignant tumor cells. After transient glucose "starvation" for rare tumor cells, they were co-incubated with 2-NBDG for a period of time, washed with ice PBS, and the fluorescence signal emitted from the cells ingesting 2-NBDG was detected by fluorescence microscopy.

The present invention is mainly against several technical challenges in the current field of CTC detection: (1) The lack of a method for the rapid and accurate identification of CTCs. The standard used by Johnson & Johnson's commercialized system CellSearch is EpCAM-positive CK-positive CD45-negative DAPI-positive, but the cells can only be identified as epithelial cells instead of tumor cells, it usually requires more complicated methods such as sequencing, FISH, etc. to further identify and isolate the benign and malignant cells, lacking a simple and rapid method; (2) due to the number of blood cells is large and CTC is very rare in blood or pleural fluid samples, the traditional methods for detecting CTCs are generally the following steps: enrichment and then detection, but it is often complicated and easy to lose CTC during the enrichment process, thereby reducing the detection rate of CTC; (3) Sequencing of CTCs is very important to guide the use of drugs, so that it is therefore necessary to be able to reliably take out CTCs for subsequent analysis after CTCs have been identified.

For the technical challenge 1, the method of metabolic activity detection is used in the present invention to identify tumor cells, that is, using the principle that the uptake of glucose for tumor cells is much higher than that in normal cells, and the detection of expression of leukocyte marker CD45 is further combined to improve the accuracy of identification. This method is simple, inexpensive, and allows rapid screening for large numbers of cells.

For the technical challenge 2, since the detection method of glucose uptake is simple and rapid, combination with a high-speed fluorescence imaging system can detect a large number of cells in a short time, and it is possible to detect the sample without enrichment or after only simple enrichment. For example, for pleural effusion samples, glucose uptake detection on all cells can usually be performed without enrichment to identify tumor cells therein, since the cells in the sample themselves are small. For blood samples, after the lysis of red blood cells, a simple negative selection is performed by magnetic balls labeled with CD45 antibody to reduce the number of cells, glucose uptake assays are performed on all remaining cells to identify CTCs.

For technical challenge 3, a microwell array chip is designed in the present invention to allow cells to enter the hole for detection. Since each microwell is addressable, the coordinates of the cells in the microwell are also fixed. Once identified as a tumor cell, the cell can be found based on its coordinates and taken out from the microwells by manual or automated microscopic manipulation uptake.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A method for detecting metabolic activity of a circulating tumor cell, which comprises the steps of:
   (a) enriching and isolating a circulating tumor cell or CTC from a peripheral blood sample, thereby obtaining the isolated circulating tumor cell;
   (b) placing the circulating tumor cell isolated in the above step in a microwell array chip, so that there is at most one circulating tumor cell in each microwell of the microwell array chip;
   (c) resuscitating the circulating tumor cell in the above step, thereby obtaining the resuscitated circulating tumor cell;
   (d) culturing the resuscitated circulating tumor cell in the presence of a glucose analogue carrying a detectable label; and
   (e) detecting uptake of the glucose analogue carrying the detectable label by the circulating tumor cell to qualitatively or quantitatively determine metabolic activity and/or malignancy degree of the circulating tumor cell; wherein the glucose analogue is 2-NBDG.

2. The method of claim 1, which further comprises a step of starving the resuscitated circulating tumor cell between step (c) and step (d).

3. The method of claim 2, wherein the starvation treatment is to place the circulating tumor cell under a culture condition of low glucose concentration or glucose-free for a period of time.

4. The method of claim 1, wherein the resuscitation comprises one or more treatment selected from the group consisting of:
   (i) resuscitation in a physical environment, wherein the physical environment refers to a low oxygen environment;
   (ii) resuscitation in a chemical environment, wherein the chemical environment refers to culturing in a cell culture medium containing a cytokine which comprises an epidermal growth factor, a fibroblast growth factor, or a combination thereof; and
   (iii) resuscitation in a tumor cell culture supernatant.

5. The method of claim 1, wherein the detectable label comprises a chemically modified group.

6. The method of claim 1, wherein in step (a), enriching and isolating the circulating tumor cell from peripheral blood is performed by an immunomagnetic bead method, wherein the immunomagnetic bead is loaded with an antibody that specifically binds to a tumor surface antigen.

7. The method of claim 1, wherein the number of circulating tumor cell enriched and isolated from a peripheral blood sample in step (a) is n1; in step (b), the number of microwell of the microwell array chip is n2; and the ratio of n2/n1 is ≥10.

8. The method of claim 1, wherein in step (e), the excess glucose analog is washed, and the ability of glucose uptake by the circulating tumor cell is characterized according to signal of the glucose analog uptaken into the circulating tumor cell.

9. The method of claim 1, wherein in steps (b) to (e), the cell surface of the circulating tumor cell is bound with a magnetic bead.

10. The method of claim 4, wherein low oxygen environment is an environment where oxygen is present in a concentration of less than 10% by volume.

* * * * *

SEQUENCE LISTING

<160> NUMBER OF SEQ ID NOS: 1

<210> SEQ ID NO 1
<211> LENGTH: 12
<212> TYPE: DNA
<213> ORGANISM: artificial seuqence
<220> FEATURE:
<223> OTHER INFORMATION: the second exon of the oncogene KRAS

<400> SEQUENCE: 1
gagcttgtgg cg                                                         12